(12) United States Patent
Webster et al.

(10) Patent No.: US 9,259,005 B2
(45) Date of Patent: Feb. 16, 2016

(54) ANTIPATHOGENIC SURFACES HAVING SELENIUM NANOCLUSTERS

(75) Inventors: Thomas J. Webster, Barrington, RI (US); Phong Anh Tran, Providence, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 13/809,611

(22) PCT Filed: Jul. 13, 2011

(86) PCT No.: PCT/US2011/043846
§ 371 (c)(1),
(2), (4) Date: May 8, 2013

(87) PCT Pub. No.: WO2012/009433
PCT Pub. Date: Jan. 19, 2012

(65) Prior Publication Data
US 2013/0236523 A1  Sep. 12, 2013

Related U.S. Application Data

(60) Provisional application No. 61/363,828, filed on Jul. 13, 2010.

(51) Int. Cl.
*A61K 33/04* (2006.01)
*A01N 59/02* (2006.01)

(52) U.S. Cl.
CPC ............ *A01N 59/02* (2013.01); *A61K 33/04* (2013.01)

(58) Field of Classification Search
CPC .................. A01N 59/02; A61K 33/04
See application file for complete search history.

(56) References Cited

U.S. PATENT DOCUMENTS

2002/0015697 A1*  2/2002  Beckman et al. ............ 424/94.4
2006/0246105 A1* 11/2006  Molz et al. ................... 424/423
2007/0224275 A1*  9/2007  Reid et al. .................... 424/489

OTHER PUBLICATIONS

Tran et al., Selenium Nanocluster Coatings for Anti-Cancer Orthopedic Applications, 2009 IEEE 35th Annual Bioengineering Conference, 2 pages, published Apr. 2009.*
Tran, Phong, A. et al, Opportunities for Nanotechnology-Enabled Bioactive Bone Implants, Journal of Materials Chemistry, 2009, Issue 18, vol. 19, pp. 2653-2659.
International Search Report and Written Opinion for International Application No. PCT/US2011/043846 dated Dec. 12, 2012.
International Preliminary Report on Patentability for International Application No. PCT/US2011/043846 dated Jan. 24, 2013.

* cited by examiner

*Primary Examiner* — Kyle Purdy
(74) *Attorney, Agent, or Firm* — Banner & Witcoff, Ltd.

(57) ABSTRACT

The present invention is directed to methods for inhibiting growth of pathogens and to substrates with selenium nanoparticles or selenium nanoclusters having antipathogenic properties.

15 Claims, 18 Drawing Sheets

ANTIPATHOGENIC SURFACES HAVING SELENIUM NANOCLUSTERS

RELATED APPLICATION DATA

This application is a National Stage Application under 35 U.S.C. 371 of co-pending PCT application PCT/US2011/043846 designating the United States and filed Jul. 13, 2011; which claims the benefit of U.S. provisional patent application No. 61/363,828 and filed Jul. 13, 2010 each of which are hereby incorporated by reference in their entireties.

STATEMENT OF GOVERNMENT INTERESTS

This invention was made with government support under DMI0050661 awarded by National Science Foundation (NSF). The Government has certain rights in the invention.

FIELD

The present invention relates to the field of nanotechnology and, in particular, to the surface of materials having selenium nanoparticles or nanoclusters of selenium nanoparticles. The surface of the materials exhibit antipathogenic properties. The present invention relates to non-medical applications such as in the field of textiles, fabrics, woven materials, non-woven materials where antibacterial properties are desired. The present invention also relates to the field of implants and/or medical devices, and more particularly to the modification of the surface of implants and/or medical devices using selenium nanoclusters for antipathogenic functionality, thereby lowering the risk of infection to patients into which the implant or medical device is placed or implanted.

BACKGROUND

Attachment and growth of bacteria is undesirable on surfaces of devices that are intended to be placed in the body of an individual because of the risk of infection to the individual. Such devices include needles, tubes, implants, medical devices and the like. Attachment and growth of bacteria is further undesirable on surfaces where materials or devices are prepared prior to insertion into an individual. Attachment and growth of bacteria is also undesirable on surfaces where food preparation takes place, as food can become contaminated prior to ingestion. It is therefore desirable to produce a surface where adherence and/or proliferation of bacteria is decreased thereby reducing the risk of infection. Implants with nanoscale surface features are known. See *J. Mater. Chem.*, 2009, 19, 2653-2659.

It is therefore an object of the present invention to create a surface characterized by selenium nanoparticles or selenium nanoclusters where the ability of pathogens to adhere and/or proliferate is inhibited. It is a further object to create articles such as medical devices which may or may not be incorporated into the body or implants which are intended to be placed within the human body that have or have been modified to include a surface characterized by selenium nanoparticles or selenium nanoclusters and having antipathogenic properties. It is a further object of the present invention to provide a surface or alter the surface of a substrate in a manner to reduce or inhibit pathogen adhesion and/or proliferation. These and other objects, features, and advantages of the invention or certain embodiments of the invention will be apparent to those skilled in the art from the following disclosure and description of exemplary embodiments.

SUMMARY

Embodiments of the present invention are directed to surfaces of substrates characterized by a plurality of selenium nanoparticles or selenium nanoclusters which may be clusters of selenium nanoparticles on the surface of the substrate where the surface is antipathogenic such as being antimicrobial, antibacterial, antifungal, antiyeast and the like. In certain embodiments, the ability of pathogenic microorganisms, i.e. pathogens such as microbes and/or bacteria and/or fungi and/or yeast to adhere, proliferate, be virulent and/or colonize to the surface is decreased, inhibited and/or reduced. It is to be understood that pathogenic microorganisms include microbes, bacteria, fungus and yeast specific examples of which will be readily apparent to those of skill in the art based on the present disclosure and available references. It is to be understood that the term nanoparticles and nanoclusters are used interchangeably throughout and that nanoclusters are understood to be clusters or groups of nanoparticles or the term nanocluster can also refer to a single nanoparticle, such that selenium nanoclusters can refer to a selenium nanoparticle or vice versa. The surface is referred to herein as being "antipathogenic" to the extent that the ability of pathogens to adhere to the surface is decreased thereby reducing the proliferation and amount of pathogens and thereby reducing the risk of infection or illness due to the presence of pathogens. The surface is also referred to herein as being "antipathogenic" to the extent that the surface presents a toxic environment to the pathogens such that pathogens will die or be killed or be rendered non-virulent when present on the surface, therefore resulting in reduced proliferation and amount of pathogens and reduced risk of infection or illness due to the presence of pathogens. The surface is referred to herein as being "antimicrobial" to the extent that the ability of microbes to adhere to the surface is decreased thereby reducing the proliferation and amount of microbes and thereby reducing the risk of infection or illness due to the presence of microbes. The surface is also referred to herein as being "antimicrobial" to the extent that the surface presents a toxic environment to the microbes such that microbes will die or be killed or be rendered non-virulent when present on the surface, therefore resulting in reduced proliferation and amount of microbes and reduced risk of infection or illness due to the presence of microbes. The surface is referred to herein as being "antibacterial" to the extent that the ability of bacteria to adhere to the surface is decreased thereby reducing the proliferation and amount of bacteria and thereby reducing the risk of infection or illness due to the presence of bacteria. The surface is also referred to herein as being "antibacterial" to the extent that the surface presents a toxic environment to the bacteria such that bacteria will die or be killed or be rendered non-virulent when present on the surface, therefore resulting in reduced proliferation and amount of bacteria and reduced risk of infection or illness due to the presence of bacteria. The surface is referred to herein as being "antifungal" to the extent that the ability of fungus to adhere to the surface is decreased thereby reducing the proliferation and amount of fungus and thereby reducing the risk of infection or illness due to the presence of fungus. The surface is also referred to herein as being "antifungal" to the extent that the surface presents a toxic environment to the fungus such that fungus will die or be killed or be rendered non-virulent when present on the surface, therefore resulting in reduced proliferation and amount of fungus and reduced risk of infection or illness due to the presence of fungi. The surface is referred to herein as being "antiyeast" to the extent that the ability of yeast to adhere to the surface is decreased thereby reducing the proliferation and amount of yeast and thereby reducing the risk of infection or illness due to the presence of yeast. The surface is also referred to herein as being "antiyeast" to the extent that the surface presents a toxic environment to the yeast such that yeast will die or be killed or be rendered non-virulent when present on the surface, therefore resulting in reduced proliferation and amount of yeast and reduced risk of infection or illness due to the presence of yeast. It is to be understood that the selenium nanoparticles or nanoclusters whether present on the surface of a substrate or simply as selenium nanoparticles or nanoclusters whether free or in solution or other medium for contacting microbes, bacteria, fungus, yeast or the like present an adverse environment to the growth of microbes, bacteria, fungus, yeast and the like for example by inhibiting adherence microbes, bacteria, fungus, yeast and the like to the surface and preventing growth or by being directly toxic to the microbes, bacteria, fungus, yeast or the like. It is to be understood that embodiments of the present invention allow some adherence and/or proliferation and/or existence of microbes and/or bacteria and/or fungus and/or yeast on the surface of the substrate with the selenium nanoparticles or selenium nanoclusters. The terms nanoclusters or clusters include localized concentrations of selenium on the surface of a substrate.

Embodiments of the present invention are also directed to methods of providing or increasing the concentration of selenium on the surface of a substrate. According to one embodiment, the selenium is added to the surface of the substrate in discreet nanometer scale clusters or three dimensional localized concentrations of selenium. The clusters or concentrations may be spaced apart from each other on the surface of the substrate and may result in an alteration of the surface roughness on a nanometer scale. According to an alternate embodiment, selenium is provided on the surface of a substrate, such as in the form of selenium nanoparticles. The substrate may be the surface of an article, an implant or the surface of a wound or other tissue where antimicrobial and/or antibacterial and/or antifungal and/or antiyeast properties of the selenium are desired. The substrate may have microbes or bacteria or fungus or yeast present on its surface. According to one aspect, the selenium nanoparticles inhibit proliferation or growth of microbes or bacteria or fungi or yeast or lower the amount of microbes or bacteria or fungus or yeast on the surface or otherwise increase microbe or bacteria or fungus or yeast cell death.

Embodiments of the present invention are also directed to methods of providing a substrate surface with a nanometer scale surface geometry or surface roughness. According to this aspect of the present invention, clusters of selenium are provided on the surface of the substrate. The clusters have average nanometer scale dimensions including diameter or cross section and are positioned randomly and substantially evenly on the surface of the substrate with unaltered surface between selenium nanoclusters. A nanocluster is localized to the extent that it is partially, substantially or entirely surrounded by unaltered surface of the substrate. According to one embodiment, the selenium nanoclusters are deposited from a liquid medium onto the surface of the substrate in discreet nanometer scale clusters. The clusters may be spaced apart from each other on the surface of the substrate and may result in an alteration of the surface roughness on a nanometer scale. According to one aspect, the selenium nanoclusters are adhered or affixed to the surface of the substrate such that they are not easily removed by routine wear and tear of the surface of the substrate.

Embodiments of the present invention are still further directed to methods of reducing the risk of microbial or bacterial or fungal or yeast infection from the insertion or implantation of devices into an individual. Certain embodiments of the present invention are even still further directed to methods that reduce the risk of microbial or bacterial or fungal or yeast infection from the use of surfaces that may transmit microbes or bacteria or fungus or yeast in general or such as during the processing of food or the manufacture of devices or materials intended to be inserted or implanted in an individual. According to the methods, the presence of microbes or bacteria or fungus or yeast is reduced, for example when compared to a surface lacking selenium nanoclusters, thereby reducing the risk of infection or illness due to the presence of microbes or bacteria or fungus or yeast. The mechanism for reducing the amount of bacteria or yeast on the surface can include cell death, reduced cell adhesion, reduced cell proliferation, or reduced cell differentiation.

According to certain aspects of the present invention, a substrate surface is provided that has a nanometer scale surface roughness due to the presence of discrete clusters of selenium having structural features on a nanometer scale. A substrate having the nanometer scale surface roughness provided by discrete selenium nanoclusters is characterized by the reduced adhesion and/or proliferation, and/or differentiation and/or increased microbial or bacterial or fungal or yeast cell death on the surface compared to a substrate surface lacking the selenium nanoclusters and the nanometer scale surface roughness. Accordingly, substrate surfaces of the present invention are useful to reduce the risk of microbial or bacterial or fungal or yeast infection where the substrate is inserted or implanted into an individual or otherwise comes in contact with the individual or substances to be inserted, implanted or ingested in an individual or substances in general where microbes, bacteria, fungus or yeast is not desired. According to certain aspects, a method is provided to reduce the presence of microbes or bacteria or fungus or yeast on a substrate by contacting the microbes or bacteria or fungus or yeast with selenium nanoparticles or selenium nanoclusters or by altering the surface of the substrate to include selenium nanoclusters and provide a nanometer scale surface roughness. Such an altered substrate can then be inserted or implanted into an individual and thereby also reduce the risk of microbial or bacterial or fungal or yeast infection or illness in the individual as a result of the substrate being inserted or implanted in the individual. According to an alternate aspect, a method is provided to reduce the presence of microbes or bacteria or fungus or yeast by contacting the microbes or bacteria or fungus or yeast with selenium nanoparticles or selenium nanoclusters.

According to one aspect of the present invention, a method is provided of altering the surface of a substrate by contacting the substrate with one or more selenium precursors and one or more reducing agents and allowing selenium nanoclusters to deposit or otherwise form on the surface of the substrate. The one or more selenium precursors and one or more reducing agents can be in a liquid medium and/or can be applied to the surface of the substrate using delivery, application, dispersing or coating techniques known to those of skill in the art, such as brushing, spraying, mopping, dipping, dispersing, or vapor coating. According to particular aspects of the present invention, a method is provided of altering the surface of a substrate by immersing the substrate in a solution of selenium precursors and reducing agents and allowing selenium nanoparticles or nanoclusters to deposit or otherwise form on the surface of the substrate. According to certain aspects, the density of the selenium nanoclusters on the surface of the substrate or their dimensions can be altered by varying the concentration of the precursor and the immersion time.

According to an additional embodiment, selenium nanoclusters, such as pre-formed selenium nanoclusters, can be provided on the surface of a substrate using delivery, application, dispersing or coating techniques known to those of skill in the art, such as brushing, spraying, mopping, dipping, dispersing, plasma spray deposition or vapor coating. According to this aspect, selenium nanoclusters are provided in a delivery agent such as a suspension or dispersion which is contacted to microbes, bacteria, fungus and/or yeast resulting in the reduced or inhibited proliferation or growth or amount of microbes, bacteria, fungus and/or yeast or increased microbial, bacterial, fungal or yeast cell death. According to an additional embodiment, selenium nanoparticles can be provided on the surface of a substrate using delivery, application, dispersing or coating techniques known to those of skill in the art, such as brushing, spraying, mopping, dipping, dispersing, plasma spray deposition or vapor coating. According to this aspect, selenium nanoparticles are provided in a delivery agent such as a dispersion which is contacted to microbes, bacteria, fungus and/or yeast resulting in the reduced or inhibited proliferation or growth or amount of microbes and/or bacteria and/or fungus and/or yeast or increased microbial or bacterial or fungal or yeast cell death. According to an additional embodiment, selenium nanoclusters or selenium nanoparticles can be provided to a surface of a substrate in the form of a coating adhered to the surface of the substrate. The selenium nanoclusters or selenium nanoparticles present as a coating themselves or in a coating material adhered to the surface of the substrate reduce or inhibit proliferation or growth or amount of microbes and/or bacteria and/or fungus and/or yeast or increase microbial or bacterial or fungal or yeast cell death. Methods of providing adherent coatings to substrates are known to those of skill in the art and are useful in certain embodiments of the present disclosure to provide an adherent coating of selenium nanoclusters or selenium nanoparticles on the surface of a substrate.

According to other aspects, a method is provided of inhibiting growth of microbes and/or bacteria and/or fungus and/or yeast on the surface of a substrate by providing the surface of the substrate with selenium nanoparticles or selenium nanoclusters, contacting the surface with microbes and/or bacteria and/or fungus and/or yeast or otherwise exposing the surface to microbes and/or bacteria and/or fungus and/or yeast or otherwise contacting selenium nanoparticles or selenium nanoclusters to microbes and/or bacteria and/or fungus and/or yeast already present on the surface of a substrate such that microbes and/or bacteria and/or fungus and/or yeast comes into contact with the selenium nanoparticles or selenium nanoclusters and inhibiting adherence and/or growth of microbes and/or bacteria and/or fungus and/or yeast on the surface. For purposes of the embodiments of the present invention, the step of contacting the surface with microbes and/or bacteria and/or fungus and/or yeast includes microbes and/or bacteria and/or fungus and/or yeast coming into contact with the substrate as would be common when microbes and/or bacteria and/or fungus and/or yeast is transmitted through direct touch or indirect methods such as airborne travel. According to this aspect, microbial and/or bacterial and/or fungal and/or yeast infection in an animal including a human, including the risk of microbial and/or bacterial and/or fungal and/or yeast infection, is reduced when the substrate with the selenium nanoclusters is inserted into the animal.

According to other aspects, a method is provided of inhibiting growth of pathogens such as microbes and/or bacteria and/or fungus and/or yeast by contacting the pathogens to selenium nanoparticles or selenium nanoclusters and inhibiting growth of the pathogens such as microbes and/or bacteria and/or fungus and/or yeast.

According to one aspect, an antipathogenic liquid including selenium nanoparticles or selenium nanoclusters, such as a solution, suspension, dispersion, emulsion or the like, is provided. According to this aspect, selenium nanoparticles or selenium nanoclusters are provided in a liquid medium as a solution, suspension, dispersion, emulsion, or the like. The liquid medium is dispersed, sprayed, brushed or otherwise contacted to pathogens such as microbes and/or bacteria and/or fungus and/or yeast or the surface of a substrate that may contain pathogens such as microbes and/or bacteria and/or fungus and/or yeast on the surface thereof. According to this aspect, contacting selenium nanoparticles or selenium nanoclusters to pathogens such as microbes and/or bacteria and/or fungus and/or yeast inhibits or reduces the growth of such pathogens as described herein or otherwise kills the pathogens as described herein.

Figure 11:
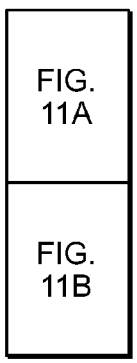
Figure 11A:
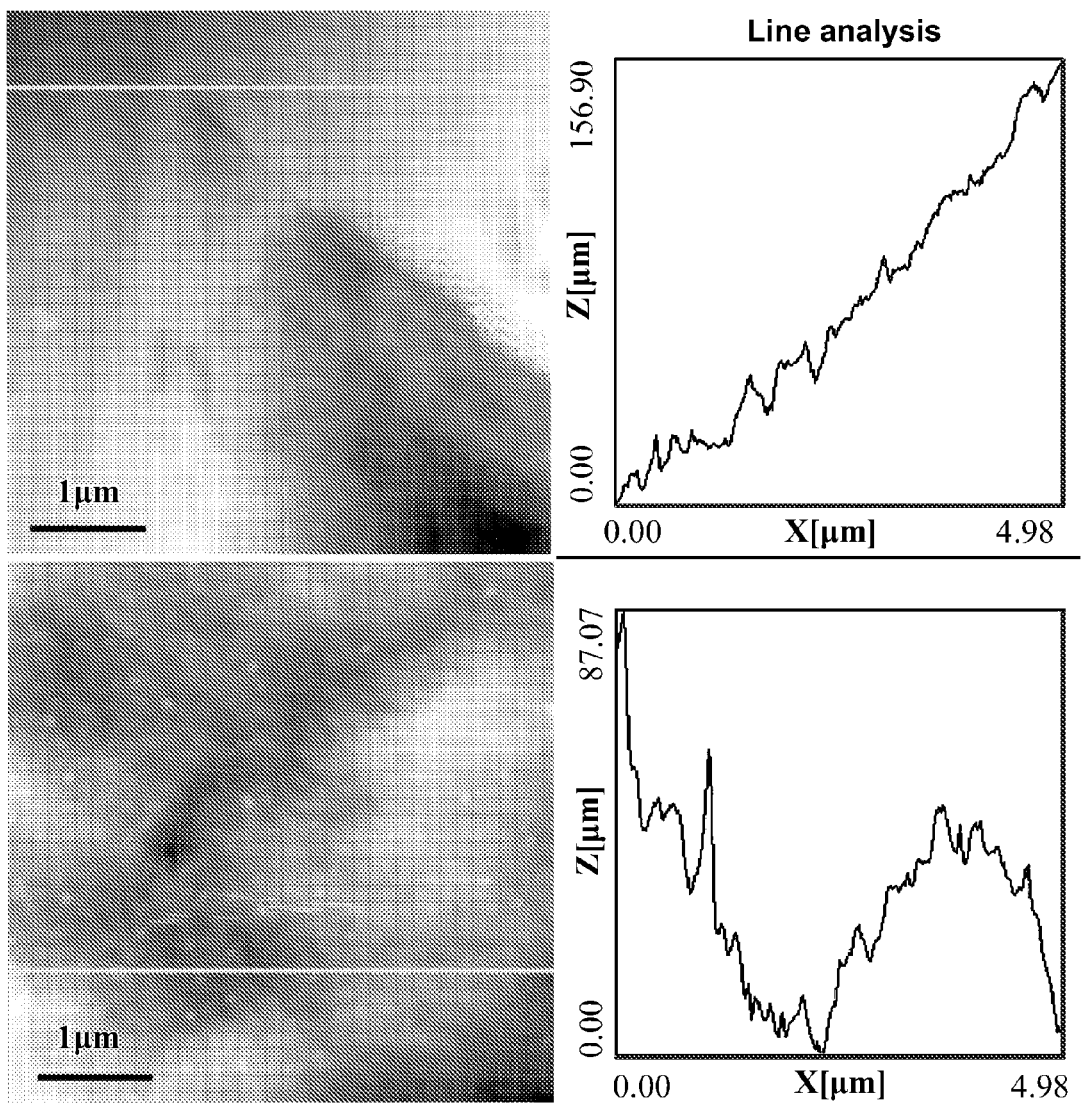
Figure 11B:
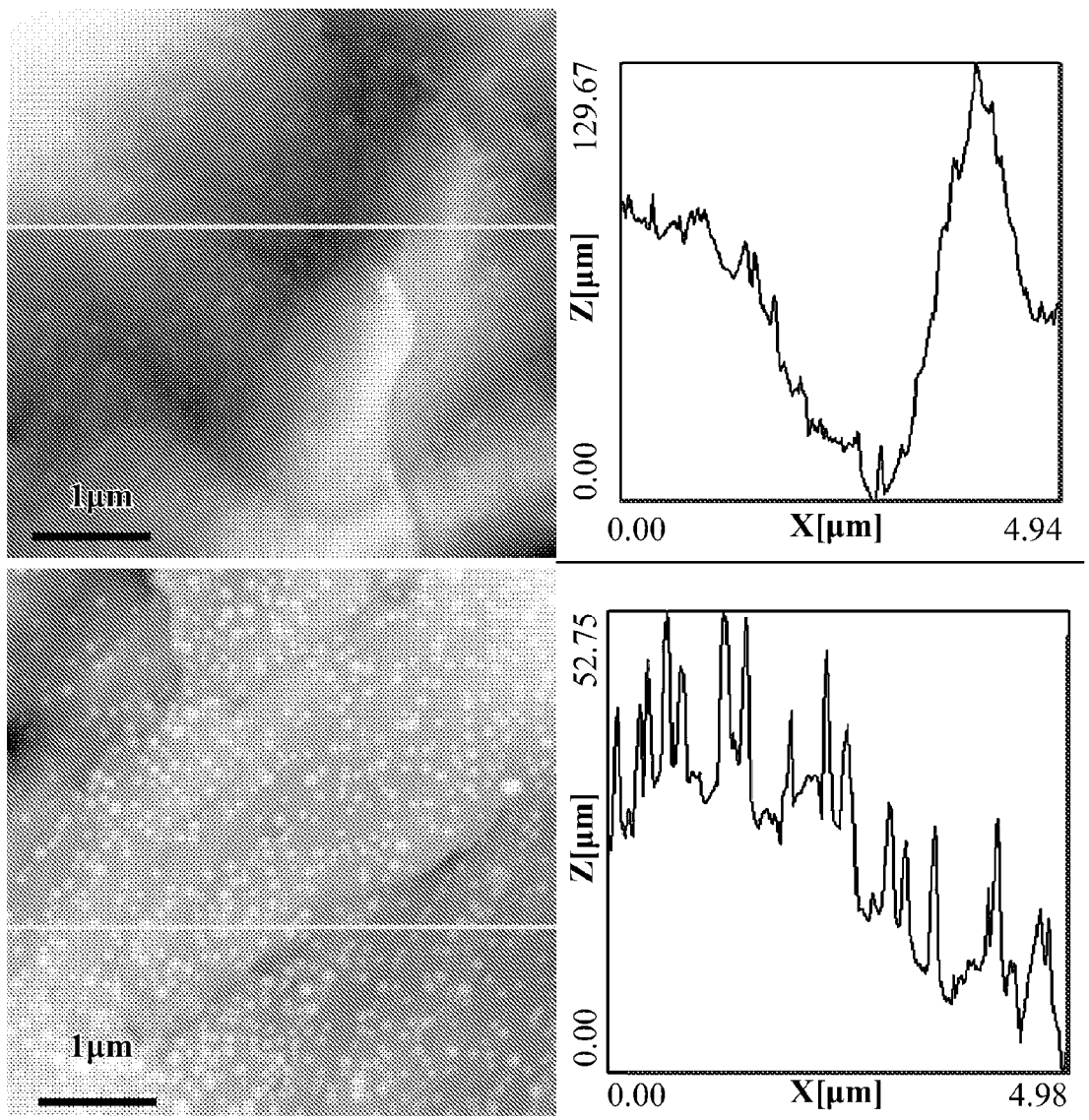

FIG. 11 depicts atomic force microscopy (AFM) images of uncoated, low density selenium nanocluster coated, medium density selenium nanocluster coated and high density selenium nanocluster coated titanium showing increasing nanoscale roughness with increasing coating density.

Figure 12:
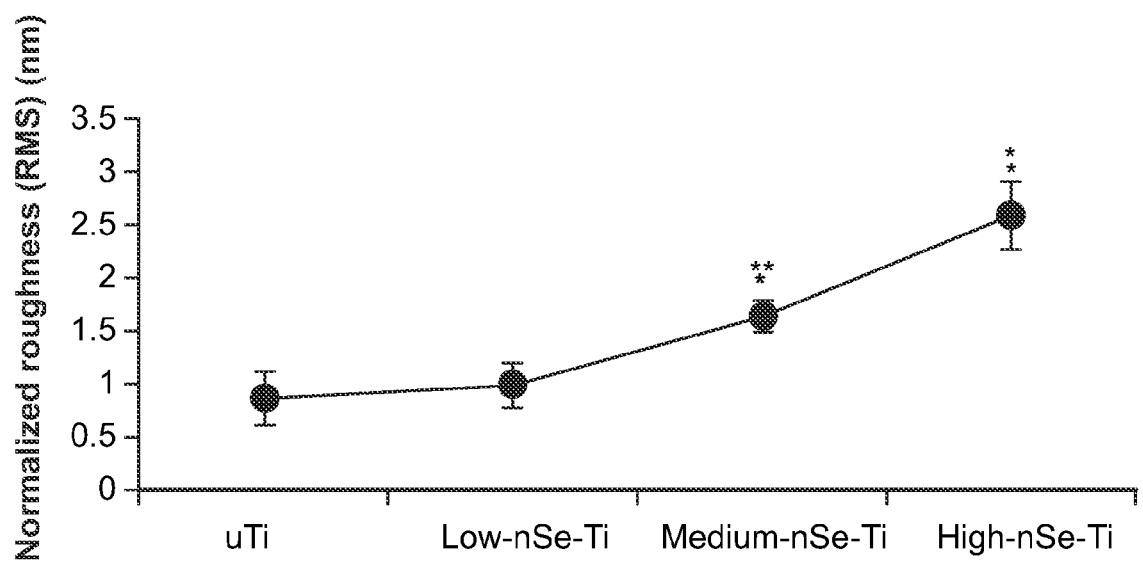

FIG. 12 is a graph depicting normalized root mean square (RMS) roughness obtained from AFM image analysis of uncoated, low density selenium nanocluster coated, medium density selenium nanocluster coated and high density selenium nanocluster coated titanium showing increasing nanoscale roughness with increasing coating density.

Figure 13:
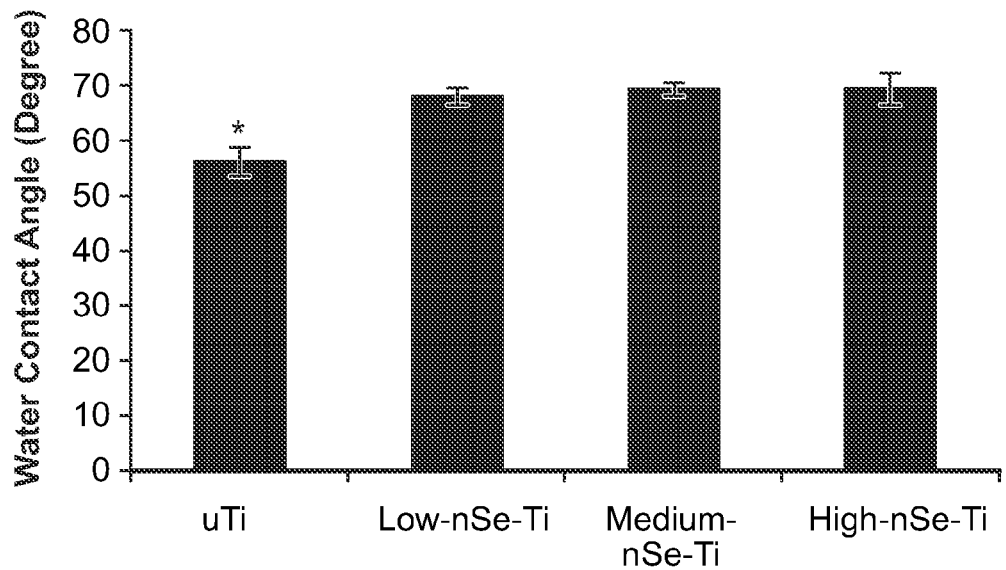

FIG. 13 is a graph depicting water contact angles of uncoated, low density selenium nanocluster coated, medium density selenium nanocluster coated and high density selenium nanocluster coated titanium showing increased water contact angle on all selenium nanocluster coated titanium substrates as compared to the uncoated substrate.

Figure 14:
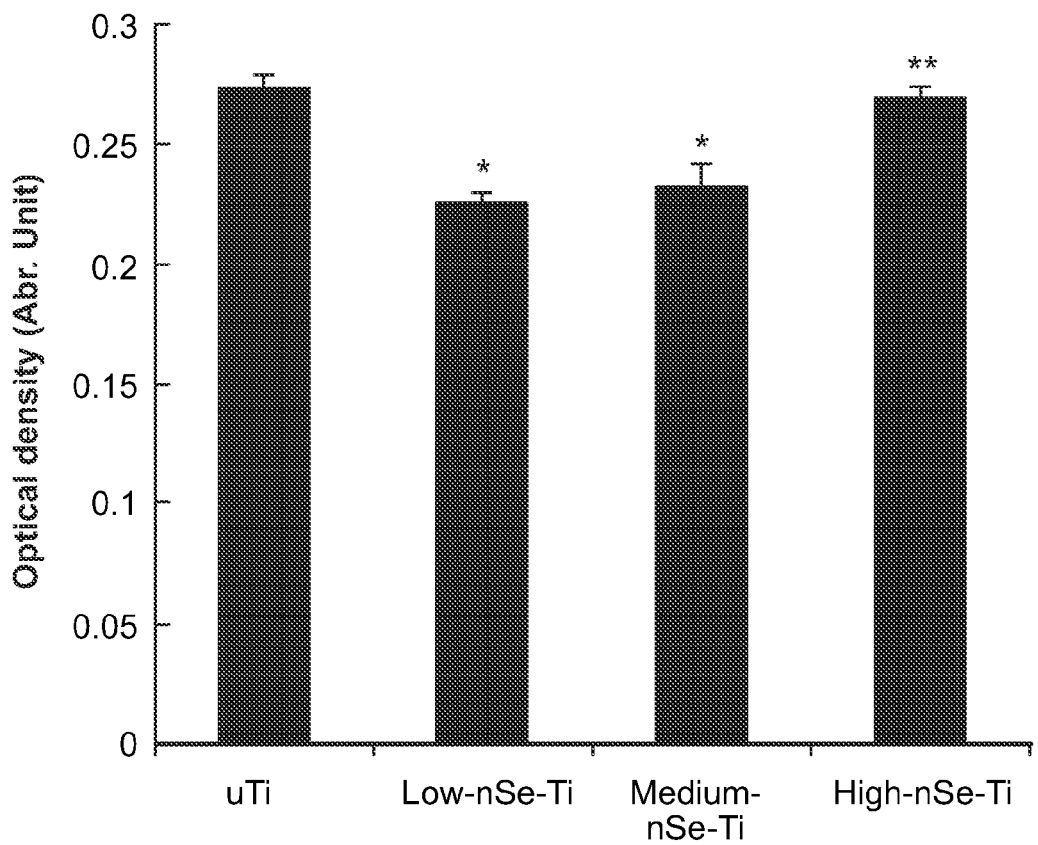

FIG. 14 is a graph depicting *S. epidermidis* optical densities after 3 days on uncoated and selenium-nanocluster-coated titanium substrates at low, medium and high nanocluster densities. The low and medium nanocluster densities exhibited statistically significant decreased bacterial densities.

Figure 15:
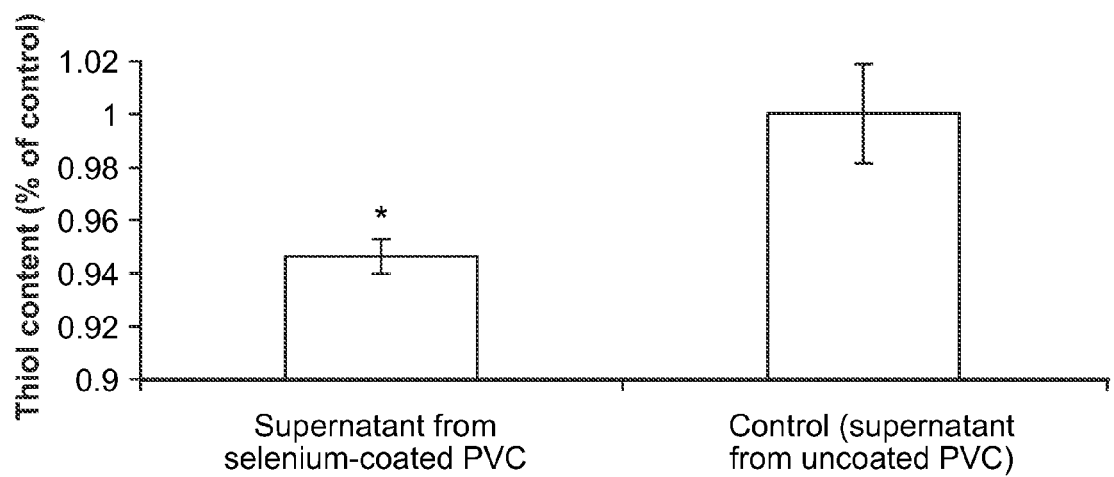

FIG. 15 is a graph depicting decreased intracellular thiol level in *S. aureus* cultured in the supernatant from selenium-coated PVC compared to control. Data=mean±standard error of the mean; N=3; * $p<0.05$ compared to the control.

Figure 16:
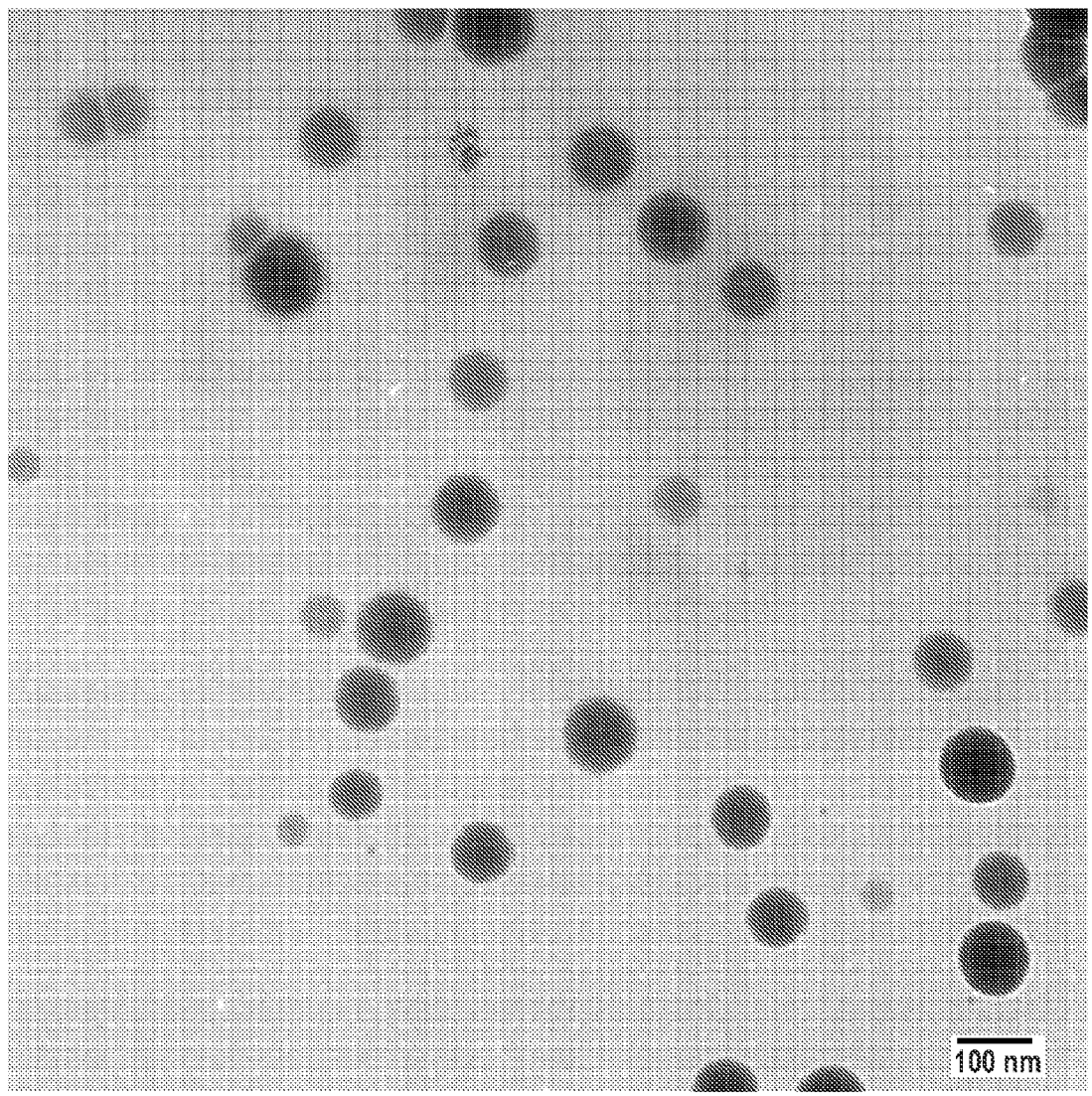

FIG. 16 is a TEM image of selenium nanoparticles stabilized in BSA and dispersed in water. Selenium nanoparticles had average sizes of approximately 100 nm.

Figure 17:
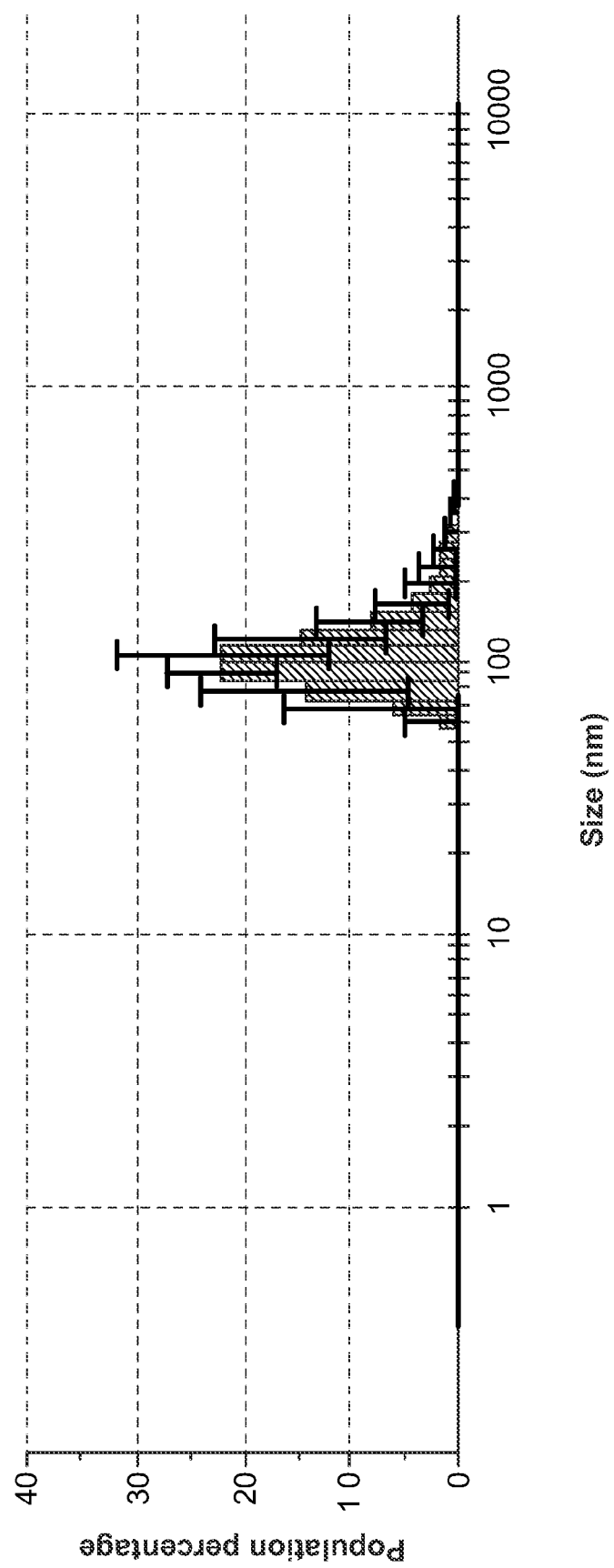

FIG. 17 is a size-distribution profile of selenium nanoparticles in solution as measured by the dynamic light scattering technique. Particle sizes centered around 100 nm.

Figure 18:
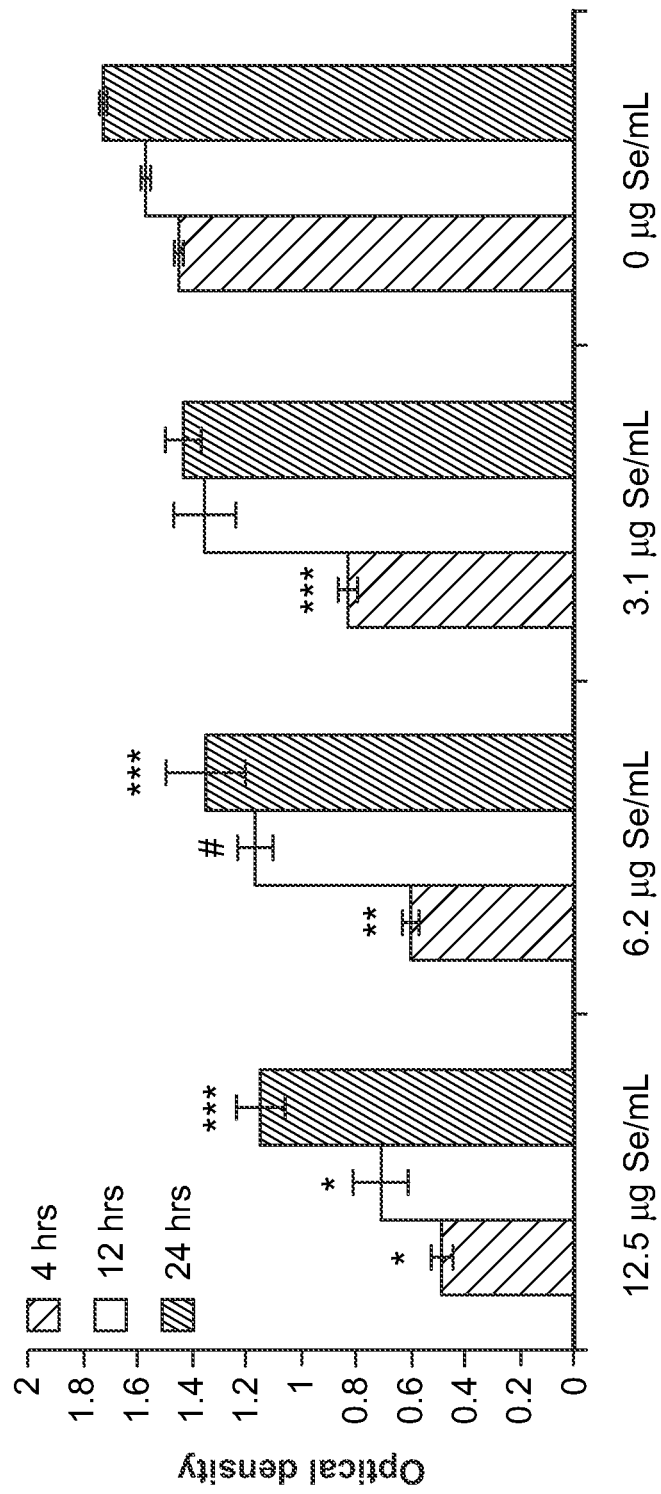

FIG. 18 is a graph showing inhibited growth of *S. aureus* in the presence of selenium nanoparticles at all three selenium nanoparticle concentrations: 12.5 μg/mL, 6.2 μg/mL and 3.1 μg/mL at 4 hrs, 12 hrs and 24 hrs. Data=mean±standard error of the mean, N=3. * $p<0.05$ compared to bacteria treated with 6.2 μg Se/mL, 3.1 μg Se/mL and control (0 μg Se/mL) (compared at same time period);  $p<0.05$ compared to bacteria treated with 3.1 μg Se/mL and control (0 μg Se/mL) (compared at same time period); * $p<0.05$ compared to control (compared at same time period); # $p<0.05$ compared to control (compared at same time period). Dose-dependent inhibition was observed at 4 hrs and 12 hrs.

Figure 19:
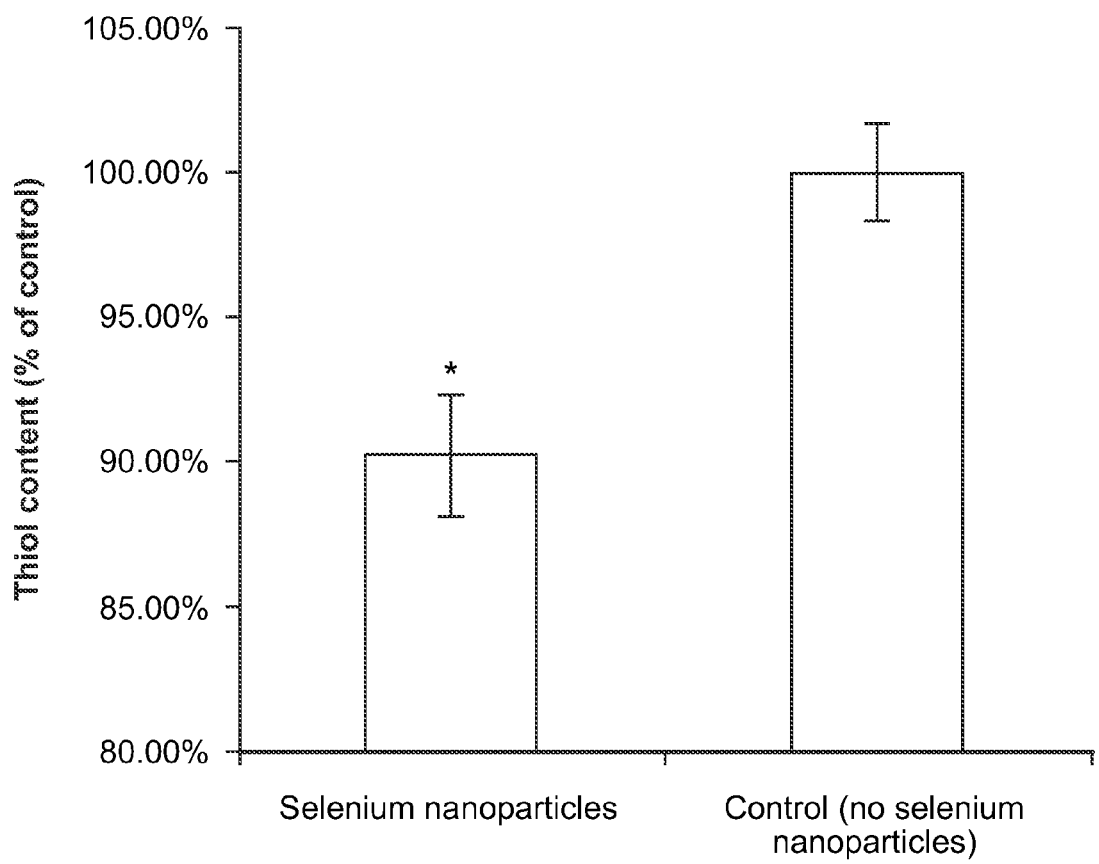

FIG. 19 is a graph showing decreased intracellular thiol levels in *S. aureus* cultured with selenium nanoparticles compared to the control (i.e., *S. aureus* cultured in TSB without selenium nanoparticles). Bacteria were cultured at a density of 50,000 cells/mL for 4 hrs in either TSB or TSB added with selenium nanoparticle (at a concentration of 3.1 μg/mL). Data=mean±standard error of the mean; N=3; * $p<0.05$.

Figure 20:
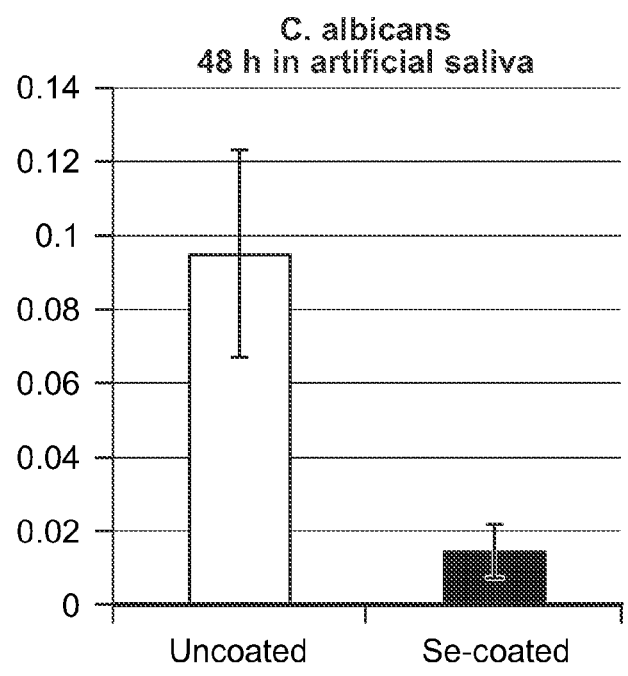

FIG. 20 is a graph showing decreased yeast populations on a PVC coated with selenium compared to uncoated PVC.

DETAILED DESCRIPTION OF CERTAIN EXEMPLARY EMBODIMENTS

Embodiments of the present invention are based on the discovery that surfaces having selenium nanoclusters desirably reduce adhesion and/or growth of pathogens such as microbes and/or bacteria and/or fungus and/or yeast. It is to be understood that microbes and/or bacteria and/or fungus and/or yeast are singly or collectively referred to herein as a pathogen or pathogens. Since the amount of microbes and/or bacteria and/or fungus and/or yeast on the surface of the substrate is reduced, the risk of microbial and/or bacterial and/or fungal and/or yeast infection or illness to an individual coming in contact with the substrate is also reduced according to certain embodiments of the present invention. It is to be understood that one of skill in the art will readily envision species of pathogens such as microbes, bacteria, fungi and yeast based on the present disclosure using standard references. Bacteria within the scope of the present disclosure include *Staphylococcus aureus, Staphylococcus epidermidis, Pseudomonas aeruginosa*, MRSA, *E. coli*, candida (yeast), *Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium, tuberculosis, Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium, Enterobacteriaceae, Staphylococcus saprophyticus* and the like. The above list is intended to be exemplary and not exhaustive. One of skill in the art will readily be able to identify additional bacteria within the scope of the present disclosure. Yeast within the scope of the present disclosure include *Cryptococcus neoformans, S. cerevisiae, Rhodotorula rubra, Torulopsis* and *Trichosporon cutaneum, Schizosaccharomyces pombe, Saccharomyces pastorianus, S. carlsbergensis, S. boulardii* and *C. albicans*. The above list is intended to be exemplary and not exhaustive. One of skill in the art will readily be able to identify additional yeast within the scope of the present disclosure.

Embodiments within the scope of the present invention include substrates that are capable of supporting selenium nanoclusters. The selenium nanoclusters can be deposited or grown or formed directly on the substrate material to create nanometer scale surface roughness. The selenium nanoclusters may be distributed uniformly and randomly across the surface of the substrate as discrete islands of nanoclusters. Substrate surfaces having selenium nanoclusters thereon can be referred to as being coated with selenium nanoclusters. Alternatively, a coating or seed material may be added onto which the selenium nanoclusters can nucleate and grow. With each of the above embodiments, the result is a substrate with a surface of selenium nanoclusters.

Substrates within the scope of the present invention can be fashioned from any material where the presence of microbes, or bacteria or fungus or yeast is undesirable. Such substrates and materials include fabrics, fibers, carbon fibers, fiber glass, woven materials, nonwoven materials, filters, filter materials, building materials etc. where the presence of microbes, or bacteria or fungus or yeast is undesirable. Additionally, substrates within the scope of the present invention can be fashioned from any material that can support or be altered to support selenium nanoparticles or selenium nanoclusters. In a particular embodiment, substrates can include any materials on which selenium nanoparticles or selenium nanoclusters can be deposited or that are susceptible of being nucleated with elemental selenium from liquid medium including a selenium precursor and a reducing agent. Suitable materials include fabrics, metals, polymers, ceramics and composites thereof and the like. Metals according to the invention include titanium, aluminum, platinum, niobium, tantalum, tin, nickel, cobalt, chromium, molybdenum, stainless steel, nitinol, Ti6Al4V, SiN, CoCrMo, zinc, silver, gold and alloys thereof and the like. The above list is intended to be exemplary and not exhaustive. One of skill in the art will readily be able to identify additional metals and metal alloys within the scope of the present disclosure. Polymers according to the invention include polycarbonate, polyethyleneimine, isoplast, polyvinyl chloride, silicone, polyurethane, polyether imide, polycaprolactone, poly-lactic-co-glycolic acid, poly-lactic acid, poly-glycolic acid, polyethylene, polyethylene glycol, polydimethylsiloxane, polyacrylamide, polypropylene, polystyrene, polyether ether ketone (PEEK), ultra high molecular weight polyethylene (UHMWPE), hydrogels, and composites thereof and the like. The above list is intended to be exemplary and not exhaustive. One of skill in the art will readily be able to identify additional polymers within the scope of the present disclosure. Ceramics according to the invention include alumina, titania, hydroxyapatite, silica, calcium phosphates, bone cements, metal oxides and composites therefore and the like. The above list is intended to be exemplary and not exhaustive. One of skill in the art will readily be able to identify additional ceramics within the scope of the present disclosure. According to a particular embodiment, polymers that are used to fashion devices to be inserted or implanted into an individual, such as polyvinyl chloride, polyurethanes and silicon based polymers such as silicones, are useful in the present invention. According to an additional aspect, a substrate can be a natural material such as tissue. Examples of exemplary tissues include skin, small intestine submucosa, large intestine submucosa, stomach submucosa, bladder submucosa, collagen, elastin, bone, cartilage, neural tissue, muscle tissue and the like or any other tissue where the antimicrobial or antibacterial or antifungal or antiyeast effects of selenium nanoclusters or selenium nanoparticles are desired.

Devices within the scope of the present invention that benefit from a reduction of adhesion of microbes and/or bacteria and/or fungus and/or yeast are devices that are intended to be inserted or implanted within an individual or any device where the presence of microbes or bacteria or fungus or yeast is undesired. Additional devices include those where food is prepared or where materials or devices intended to be inserted or implanted are manufactured or staged prior to use. Such devices are commonly found in food processing rooms, kitchens, manufacturing clean rooms, operating rooms and the like. Specific examples of devices intended to be inserted or implanted within an individual include endotracheal tubes, central venous, arterial, and urinary catheters, stents, dialysis tubing, orthopedic and dental implants, vascular implants, pacemaker leads, neural probes, neural catheters, wound healing devices, skin patches, hernia meshes, spinal implants and the like. Specific examples of devices where food is to be prepared or materials or devices intended to be inserted or implanted are manufactured or staged prior to use such as in an operating room, include table tops, countertops, trays, plastic cutting boards and the like.

According to certain aspects of the present invention, the surface of the substrate can be altered by the addition of selenium nanoclusters to create a nanoscale surface roughness, to increase or decrease surface hydrophilicity and/or to confer antimicrobial and/or antibacterial and/or antifungal and/or antiyeast properties. A selenium nanocluster is characterized as a discrete amount of selenium, such as elemental selenium, accumulated, deposited, nucleated, formed or agglomerated at a particular location over a given surface area of the substrate.

A selenium nanocluster is a physical structure having nanometer scale dimensions such as diameter, length, width and height. The selenium nanoclusters can be approximately uniform in size or can range in size or form over a given substrate surface. The nanoclusters can take the appearance of random clusters, organized clusters or patterned clusters whether isolated or overlapping to form larger nanoclusters or regions of nanoclusters or nanoparticles. The nanocluster is generally circular, spherical or hemispherical in shape, but can be of any shape. According to another aspect of the present invention, elemental selenium nanoclusters comprised of selenium units of non-spherical or non-hemispherical shapes, including nanostructures such as nanorods, nanostars, and nanowires, and can be affixed or grown on the surface of a substrate. For example, one-dimensional selenium nanostructures can be formed by seed-mediated growth.

The dimensions such as diameter, length, width or height of the nanoclusters range between about 1 nanometer and about 1000 nanometers (1 micron) or larger. For example, the nanoclusters have dimensions, such as diameter, length, width or height of between about 10 nanometers to about 900 nanometers, about 100 nanometers to about 500 nanometers, about 1 nanometer to about 100 nanometers, about 10 nanometers to about 50 nanometers, about 1 nanometer to about 10 nanometers, about 1 nanometer to about 5 nanometers, about 10 nanometers to about 100 nanometers, and any ranges or values in between the above ranges whether overlapping or not. The distance between adjacent nanoclusters ranges between about 1 nanometer and 100,000 nanometers. For example, the distance can range between about 10 nanometers to about 90,000 nanometers, about 50 nanometers to about 50,000 nanometers, about 100 nanometers to about 10,000 nanometer, about 1 nanometer to about 100 nanometers, about 10 nanometers to about 50 nanometers, about 1 nanometer to about 10 nanometers, about 1 nanometer to about 5 nanometers, about 10 nanometers to about 100 nanometers, and any ranges or values in between the above ranges whether overlapping or not.

According to a certain embodiment, the nanoclusters are distributed randomly and generally evenly across the surface of the substrate. It is to be understood that certain nanoclusters on the surface of the substrate can contact or overlap each other. According to this aspect, nanoclusters which contact or overlap each other form islands of micrometer sized nanoclusters.

According to certain aspects of the present invention, the surface hydrophobicity, hydrophilicity and/or water contact angle of the surface can be increased or decreased with the deposition of selenium nanoclusters. The amount of change and the direction of the change (increased hydrophobicity or increased hydrophilicity) may depend on the substrate material and the amount, size or arrangement of selenium nanoclusters. According to one embodiment, changes in surface hydrophobicity, hydrophilicity or contact angle with the deposition of selenium nanoclusters influences or otherwise reduces the ability of microbes and/or bacteria and/or fungus and/or yeast to adhere and/or grow on the substrate surface.

According to certain aspects of the present invention, a method of depositing selenium nanoclusters on the surface of a substrate, such as to provide an antipathigenic substrate, is provided. According to this aspect, a substrate is immersed wholly or partly into a liquid medium including a selenium precursor and a reducing agent. The liquid medium can be a solution or a colloid. The liquid medium can include water alone or with other water miscible liquids. Alternatively, selenium nanoclusters or selenium nanoparticles can be contained in a medium and deposited, dispersed or coated on the surface of a substrate using coating or application techniques known to those of skill in the art, such as, for example, to provide an antipathogenic surface or otherwise reduce or inhibit the growth of pathogens.

Selenium precursors within the scope of the present invention include selenous acid or sodium selenite and the like. The selenium precursor can be present in a concentration of greater than about 0.00001 nM or within the exemplary range of between about 0.1 mM and about 100 mM, between about 10 mM and about 90 mM, between about 20 mM and about 80 mM, between about 30 mM and about 70 mM, or between about 40 mM and about 60 mM or any range or value in between whether overlapping or not. Reducing agents within the scope of the present invention include glutathione, hydrazine, dextrose, ascorbic acid or sodium ascorbate and the like. The reducing agent can be present in a concentration of greater than 0.00001 nM or with an exemplary range of between about 1 mM and about 50 mM, between about 10 mM and about 40 mM, between about 20 mM and about 30 mM or any range or value in between whether overlapping or not. It is to be understood that one of skill in the art can readily determine the particular desired concentration and/or desired amount of either the selenium precursor or reducing agent based upon the present disclosure.

According to certain embodiments, gamma irradiation can be applied to reduce selenium precursors.

According to certain aspects of the present invention, the liquid medium can include additional ingredients, such as bovine serum albumin and sodium hydroxide. According to this aspect of the invention, sodium selenite will react with glutathione to form a glutathione compound which then forms selenium nanoparticles that are stabilized in bovine serum albumin. According to certain further aspects of the present invention, the liquid medium can include additional ingredients, such as growth factors, cytokines, vitamins, minerals, steroids and/or pharmaceutical agents to increase tissue growth, reduce bacteria or yeast function, or reduce inflammation.

The substrate is immersed in the liquid medium for a period of time and at certain temperatures sufficient to result in the formation of selenium nanoclusters on the surface of the substrate. Suitable periods of time include between about 1 second to about two weeks or more. According to certain embodiments, immersion times range between about 2 minutes and about 8 hours, between 5 minutes and about 5 hours, about 10 minutes and about 1 hour and any immersion time or range in between whether overlapping or not. One of skill in the art will recognize that longer immersion times can result in an increased number of selenium nanoclusters and/or increased size or increased dimensions of selenium nanoclusters and/or increased density of selenium nanoclusters on the surface of the substrate. Suitable temperatures range between about 0° K (absolute zero) and the melting temperature of the substance on which selenium nanoclusters are to be deposited. According to certain embodiments, suitable temperatures include between about 0° C. and 100° C., between about 4° C. and about 80° C., between about 10° C. and about 50° C., between about 15° C. and about 40° C. and between about 20° C. and about 25° C.

In addition, the surface of the substrate can be altered by the attachment of pre-formed selenium nanoparticles or nanoclusters. According to this embodiment, preformed selenium nanoparticles or nanoclusters are contained in the liquid medium or colloid and are deposited on the surface of the substrate when immersed or contacted with the liquid medium or colloid.

According to one aspect of the present invention, the surface of a medical device is modified to include selenium nanoclusters. A medical device with such a surface according to the present invention limits, inhibits, prevents and/or reduces microbial and/or bacterial and/or fungal and/or yeast adhesion and/or growth as compared to a device without the elemental selenium. The selenium nanocluster coated medical device according to the present invention may limit, inhibit and/or reduce microbial and/or bacterial and/or fungal and/or yeast adhesion and/or growth in some cases more efficiently or effectively than silver-coated medical devices (for example, commercially available silver-coated polyvinyl chloride endotracheal tubes). According to certain aspects, the selenium nanoclusters leach selenium and/or create superoxides, nanoroughness, hydrophobicity and/or other conditions which limit bacterial and/or yeast adhesion, proliferation and/or differentiation or promote bacterial and/or yeast cell death.

Embodiments of the present invention are directed to methods of inhibiting or reducing the rate of growth of bacteria and/or yeast over a prolonged period of time. According to one embodiment, a device is provided with or altered to include selenium nanoclusters on the surface, the surface already includes or is contacted with bacteria and/or yeast, and the rate of bacterial or yeast growth is inhibited or reduced over a prolonged period of time. According to certain embodiments, the rate of bacterial or yeast growth is reduced over a prolonged period of time including hours, such as about 4 hours, about 8 hours, about 12 hours, about 24 hours, about 72 hours, etc., over a period of days, such as about 1 day, about 2 days, about 3 days, about 4 days, etc., over a period of weeks, such as 1 week, 2 weeks, 3 weeks, etc., over a period of months, such as about 1 month, 2 months, 3 months, etc., and over a period of years, such as 1 year, 2 years, 3 years, etc. It is to be understood that combinations of the above time periods are within the scope of the present invention, such as the prolonged period of time could be one week and 3 days, one month and two weeks, etc.

It is to be further understood that embodiments of the present invention include methods of permanently rendering a surface of a substrate resistant to bacterial and/or yeast growth, or permanently reducing the rate of bacterial or yeast attachment and/or proliferation. According to this aspect of the invention, the methods above for creating a selenium nanocluster surface are performed on a substrate material that retains the selenium nanoclusters or replenishes the selenium nanoclusters on the surface. This includes a surface that erodes, for example hydrolytically or enzymatically, to reveal a new layer of selenium nanoclusters underneath.

It is to be further understood that embodiments of the present invention include methods of permanently rendering a surface of a substrate resistant to bacterial and/or yeast growth. Such embodiments include the method of providing a substrate with a selenium nanoclustered surface, contacting the surface with bacteria and/or yeast, and reducing the adherence and/or growth, and/or proliferation and/or accumulation of bacteria and/or yeast on the surface of the substrate. According to this aspect of the present invention, the methods above for creating a nanostructured surface are performed on a substrate material that retains the nanostructured surface features under normal wear and tear and common environmental and/or physiological conditions. For example, creating selenium nanoclusters on a PVC material according to the methods describe herein is considered permanent insofar as the selenium nanoclusters on the surface will remain physically unaltered at temperatures and environmental conditions which do not cause the PVC material to change its structure. One such set of conditions is physiological conditions and common room temperature environmental conditions. A condition which could cause the PVC material to alter its structure include coming in contact with heat sufficient to melt and/or destroy the PVC and/or solvents which could dissolve the PVC material. According to this embodiment, the term "permanent" includes the useful life of the substrate including the selenium nanoclustered surface. So long as the selenium nanoclustered surface is capable of coming into contact with microbes and/or bacteria and/or fungus and/or yeast, and the surface retains the selenium nanoclusters, the surface is permanently rendered resistant to microbial and/or bacterial and/or fungal and/or yeast growth.

An additional embodiment of the present invention includes a method of improving resistance of a substrate to microbial and/or bacterial and/or fungal and/or yeast growth including creating a substrate surface with selenium nanoclusters, contacting the surface with microbes, bacteria, fungus and/or yeast, reducing the growth of microbes, bacteria, fungus and/or yeast, removing microbial, bacterial, fungal and/or yeast growth, and repeating the steps of contacting, reducing and removing in whole or in part any number of desired times. According to this embodiment, the substrate having the nanostructured surface is reusable in methods of reducing growth of microbes, bacteria, fungus and/or yeast or otherwise reducing the rate of growth of microbes, bacteria, fungus and/or yeast. The step of removing is accomplished by common wiping or cleaning or sterilizing techniques known to those of skill in the art.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

EXAMPLES

The following examples are set forth as being representative of the present invention. These examples are not to be construed as limiting the scope of the invention as these and other equivalent embodiments will be apparent in view of the present disclosure, figures and accompanying claims.

Example 1

Formation of Selenium Nanoclusters on Polymer Surfaces to Reduce S. aureus Adherence and Proliferation Over an 8 Hour Period Polymeric substrates of polyvinyl chloride (PVC), polyurethane (PU) and silicones in the form of discs 6 mm in diameter and approximately 2 mm in height were cut from commercial PVC endotracheal tubes, medical grade PU, and commercial silicone tracheostomy tubes. The polymeric substrates were then immersed in ethanol for 10 min, sonicated in ethanol for 10 min for sterilization and air-dried in a sterile hood overnight. Cleaned and sterilized polymeric substrates (PVC, PU, and silicone) were placed in a beaker. 10 ml of deionized water and 10 ml of 100 mM glutathione were added to the beaker followed by 10 ml of 25 mM sodium selenite ($Na_2SeO_3$). After gentle mixing, 2 ml of 1M NaOH was added to the beaker to bring the pH of the mixture into the alkaline regime. The beaker was left untouched for 10 minutes. The substrates were removed and rinsed for 24 hours in deionized water. The uncoated and coated polymeric substrates (PVC, PU, and silicone) were immersed in ethanol for 30 min for sterilization and air-dried in a sterile hood overnight.

Figure 1:
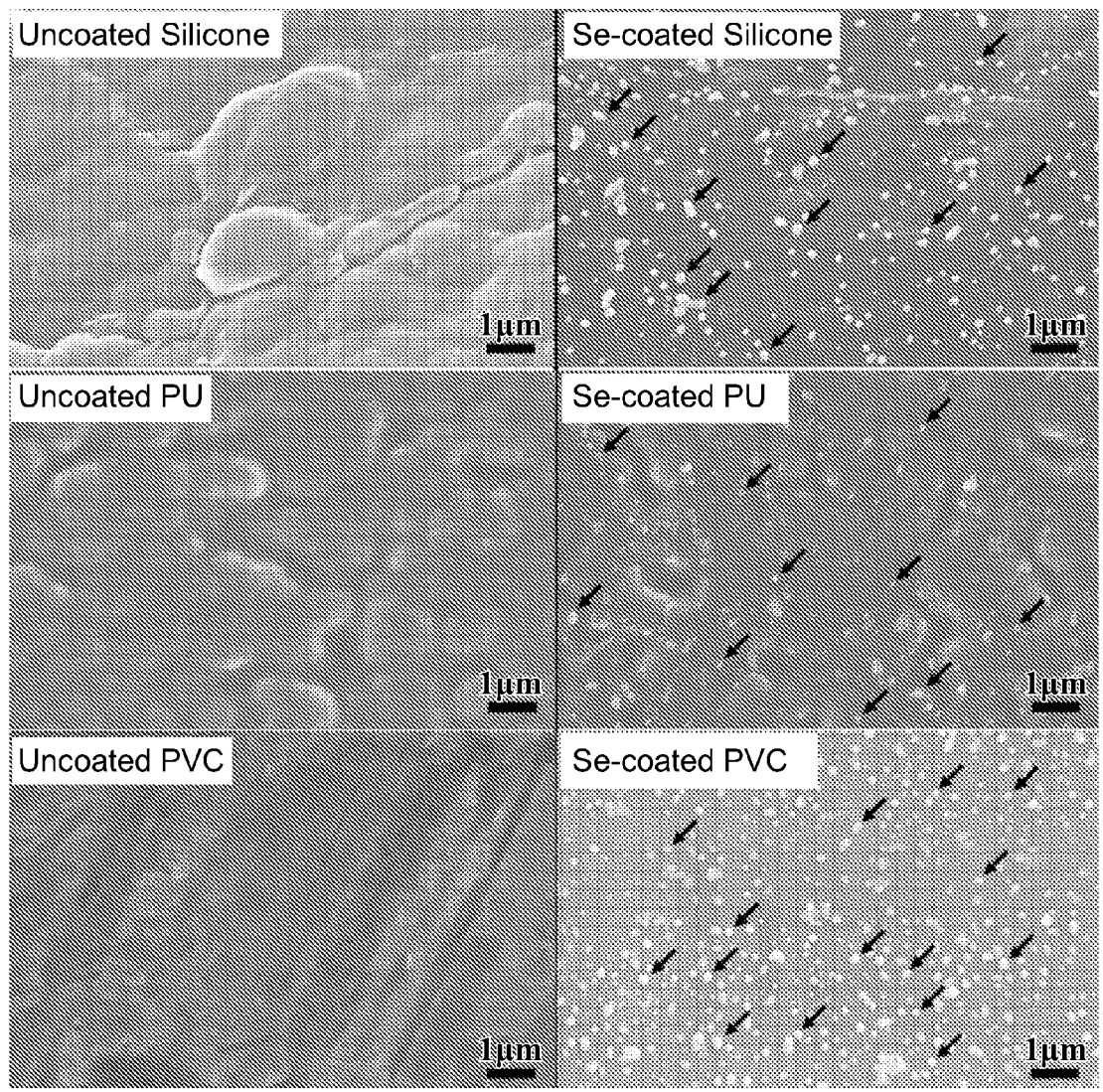
FIG. 1 depicts scanning electron microscope (SEM) images at 5 kV of untreated silicone, polyurethane and polyvinyl chloride (left panel) and selenium coated substrates (right panel).
Figure 2:
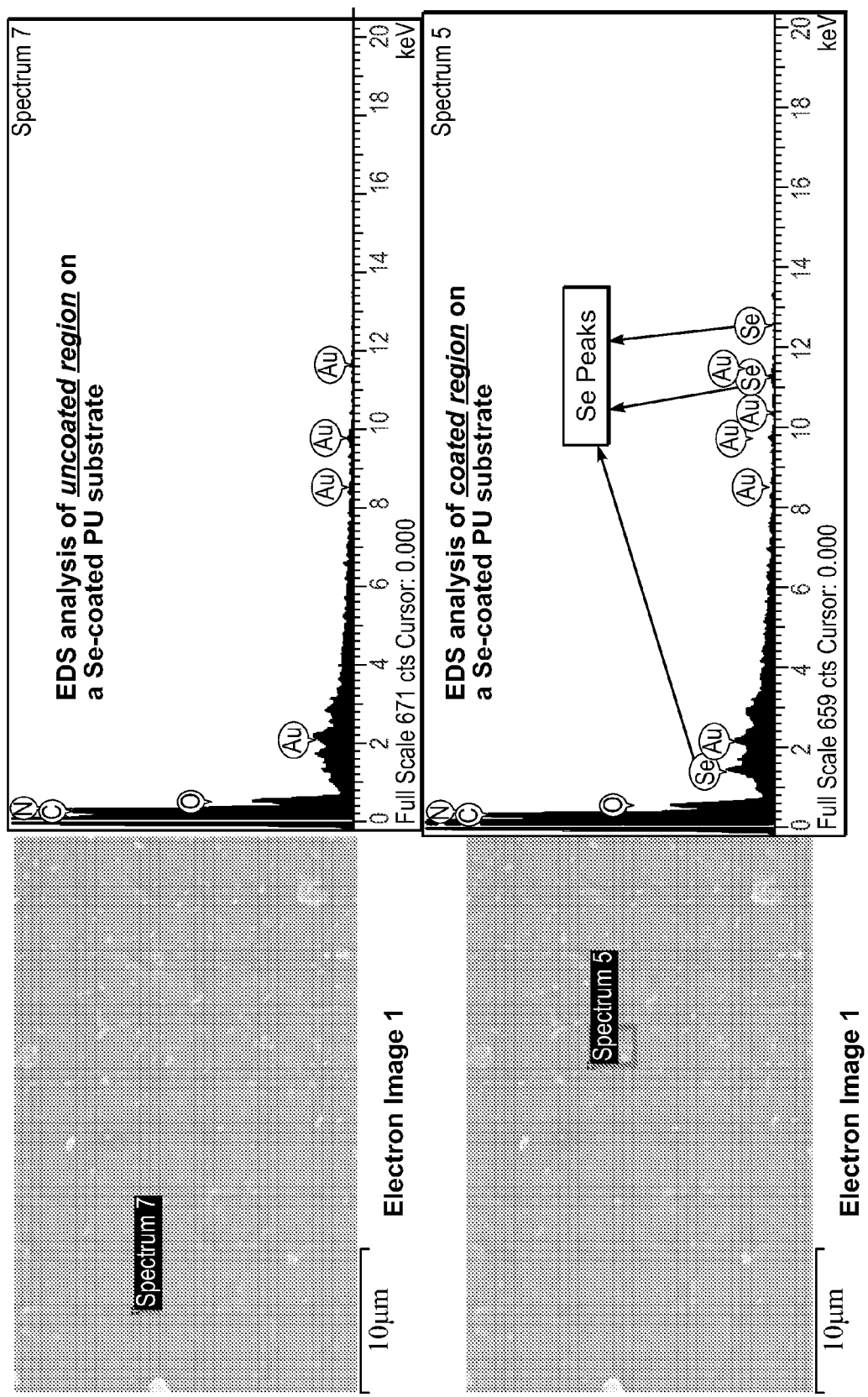
FIG. 2 depicts energy dispersed X-ray spectroscopy (EDS) spectra with an acceleration voltage of 20 kV of a region of uncoated polyurethane (top) and selenium-coated polyurethane (bottom).
Figure 3:
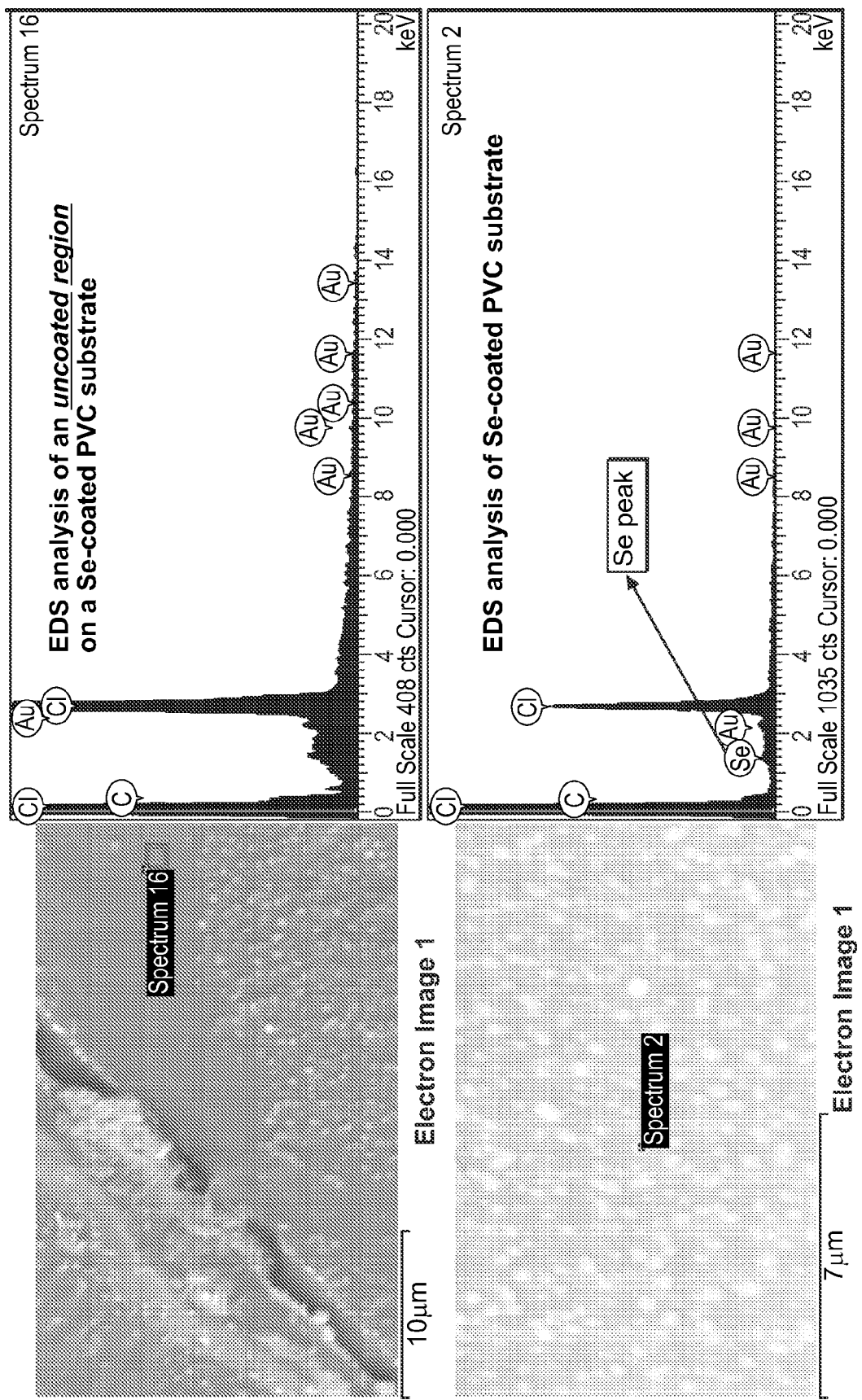
FIG. 3 depicts energy dispersed X-ray spectroscopy (EDS) spectra with an acceleration voltage of 20 kV of a region of uncoated polyvinyl chloride (top) and selenium-coated polyvinyl chloride (bottom).
Figure 4:
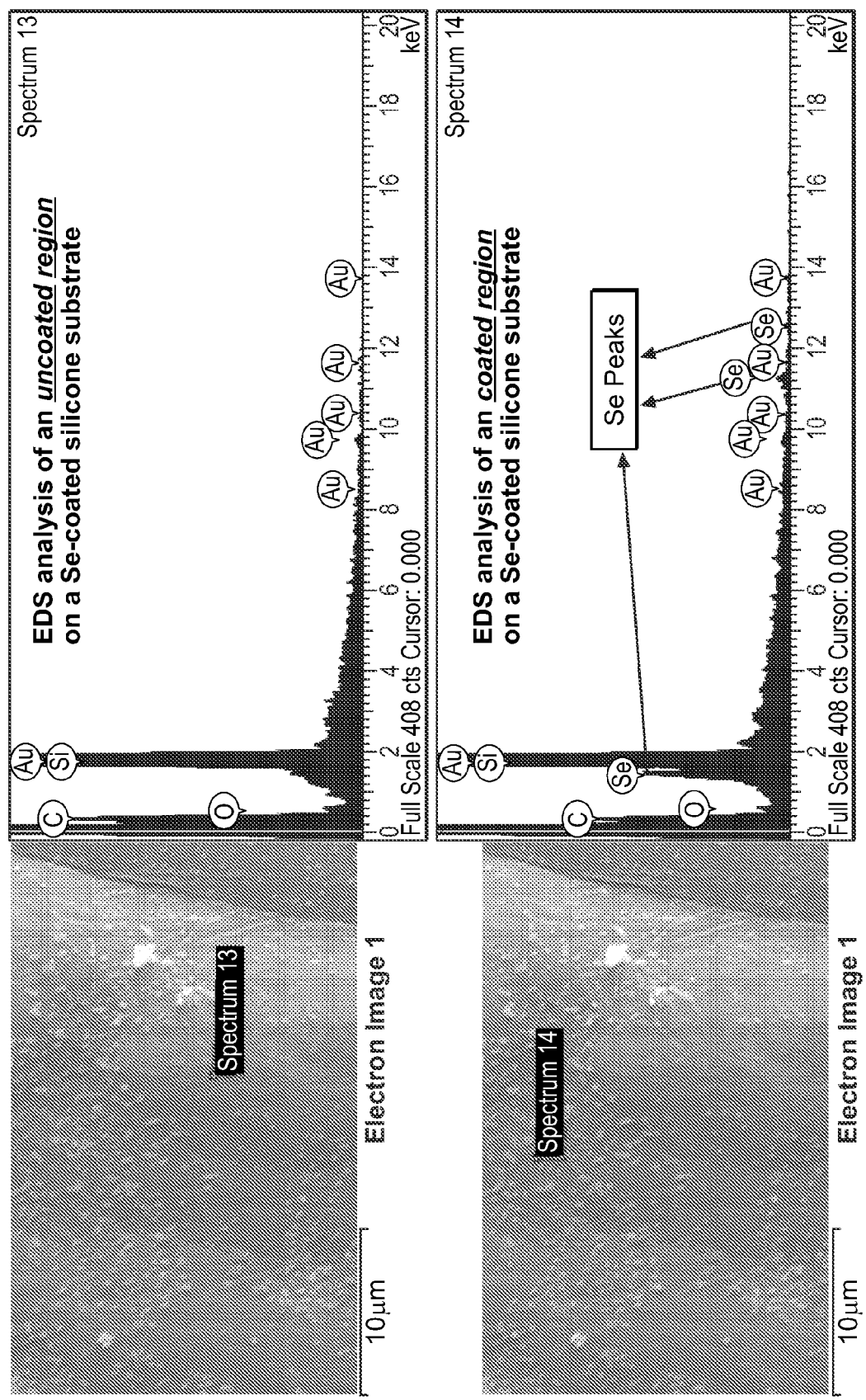
FIG. 4 depicts energy dispersed X-ray spectroscopy (EDS) spectra with an acceleration voltage of 20 kV of a region of uncoated silicone (top) and selenium-coated silicone (bottom).

Polymeric substrates (PVC, PU, and silicone) were sputter-coated with a thin layer (approximately 90 Angstroms) of palladium and observed under SEM at 5 kV. The selenium nanoclusters on the polymeric materials are visible in the SEM micrographs in FIG. 1 with arrows indicating representative nanoclusters on each of the silicone, polyurethane and polyvinylchloride substrates. For chemical characterization, energy dispersed X-ray spectroscopy (EDS) with the acceleration voltage of 20 kV was employed. FIG. 2 is an EDS graph comparing a region lacking selenium nanoclusters (uncoated) to a region including selenium nanoclusters (coated) on the surface of a polyurethane substrate. The EDS analysis confirms the presence of selenium. FIG. 3 is an EDS graph comparing a region lacking selenium nanoclusters (uncoated) to a region including selenium nanoclusters (coated) on the surface of a polyvinylchloride substrate. The EDS analysis confirms the presence of selenium. FIG. 4 is an EDS graph comparing a region lacking selenium nanoclusters (uncoated) to a region including selenium nanoclusters (coated) on the surface of a silicone substrate. The EDS analysis confirms the presence of selenium.

Figure 5:
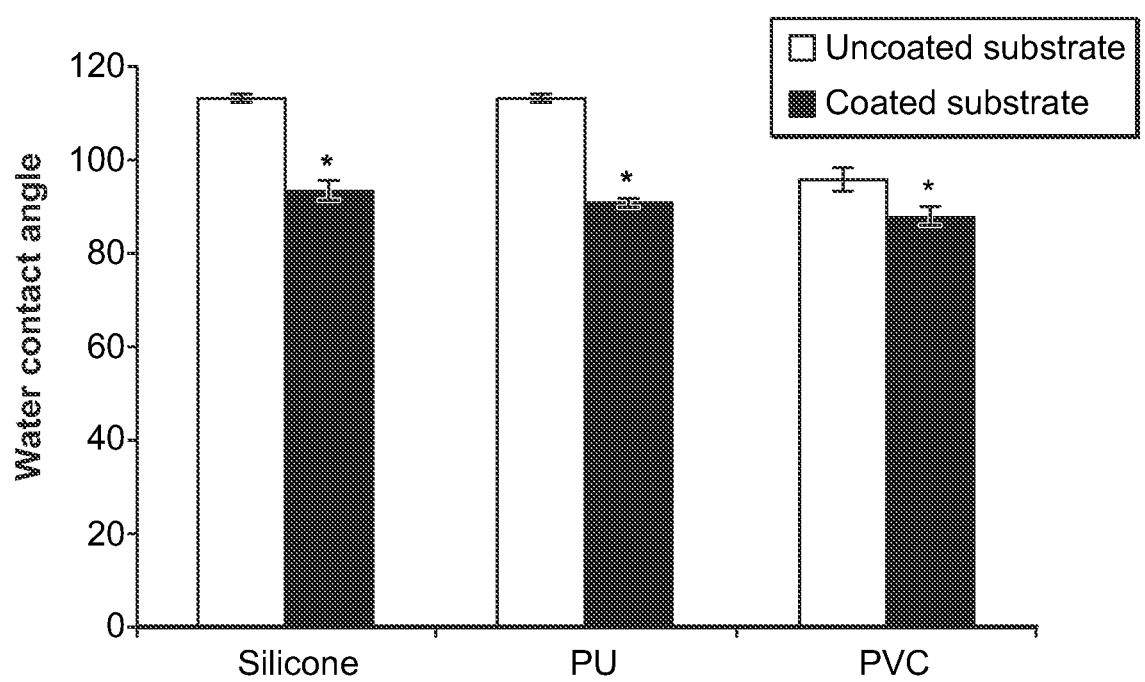
FIG. 5 is a graph depicting the water contact angles on uncoated (grey bar) and selenium-nanocluster-coated (black bar) polyurethane, polyvinyl chloride and silicone substrates.

Contact angles on the substrates with and without selenium nanoclusters were measured at room temperature by placing a 2 µL drop of deionized water on the surface of the substrate and recording the contact angle within 15 seconds. The graph in FIG. 5 shows that the water contact angle was lowered for each of the silicone, polyurethane and polyvinylchloride surfaces having selenium nanoclusters thereon compared to the surfaces without selenium nanoclusters. According to one aspect, the surfaces were rendered more hydrophilic by the selenium nanoclusters compared to the surfaces without the selenium nanoclusters.

Figure 6:
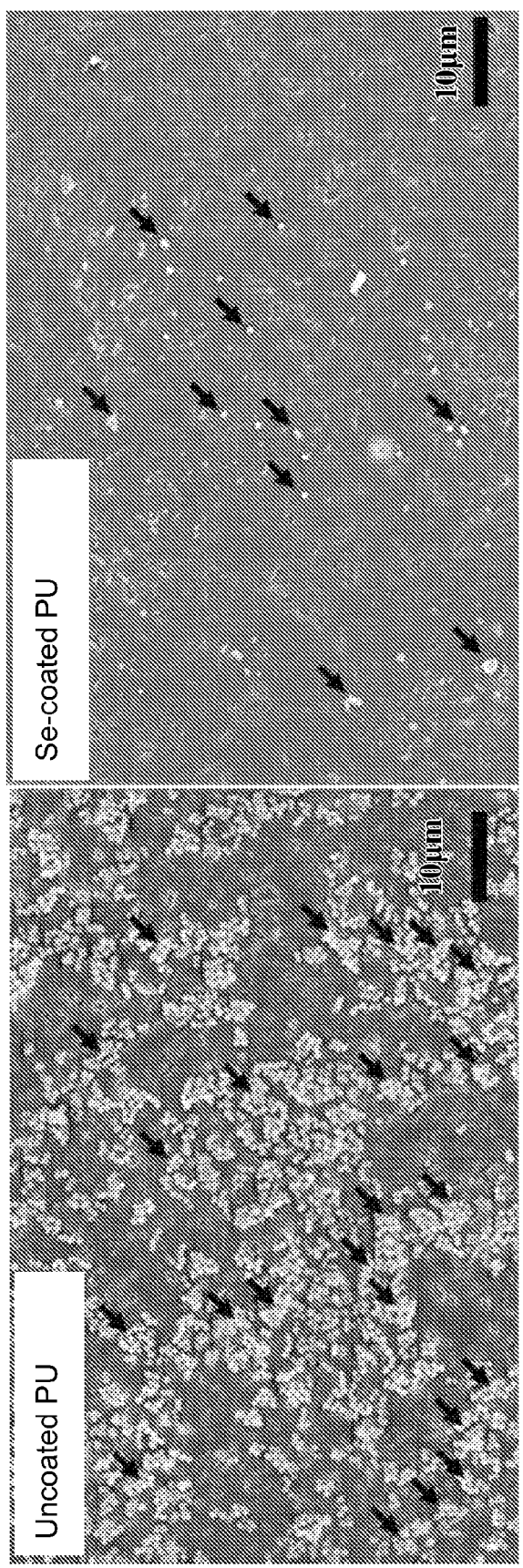
FIG. 6 depicts SEM images of uncoated (left) and selenium-coated (right) polyurethane substrates after inoculation for 8 hours at a seeding density of 20,000,000 S. aureus bacteria per well (24 well plate). Arrows indicate cells.
Figure 7:
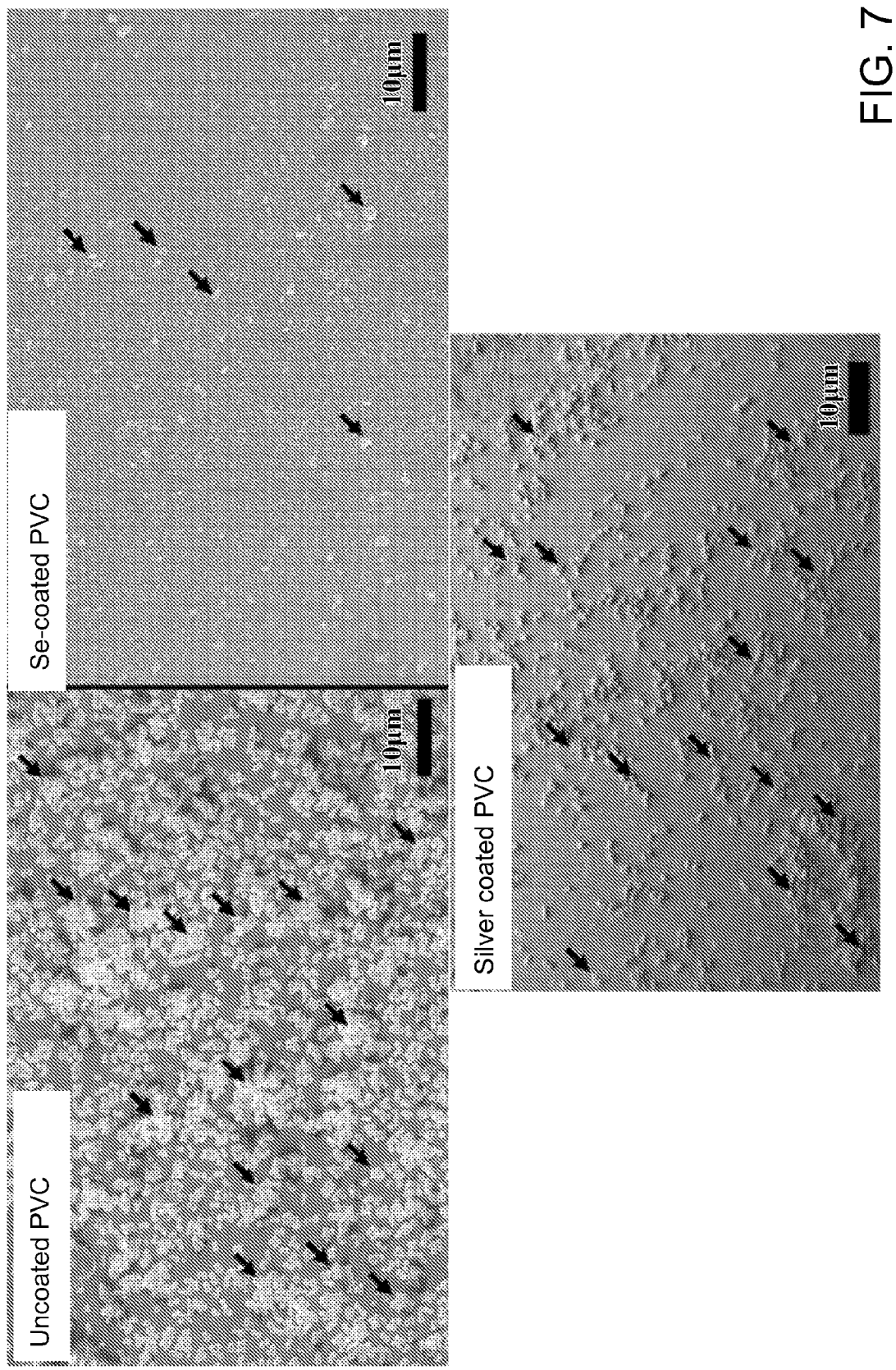
FIG. 7 depicts SEM images of uncoated polyvinyl substrates (top left), selenium-coated polyvinyl chloride substrates (top right) and commercially available silver-coated polyvinyl chloride endotracheal tubes (bottom) after inoculation for 8 hours at a seeding density of 20,000,000 S. aureus bacteria per well (24 well plate). Arrows indicate cells.
Figure 8:
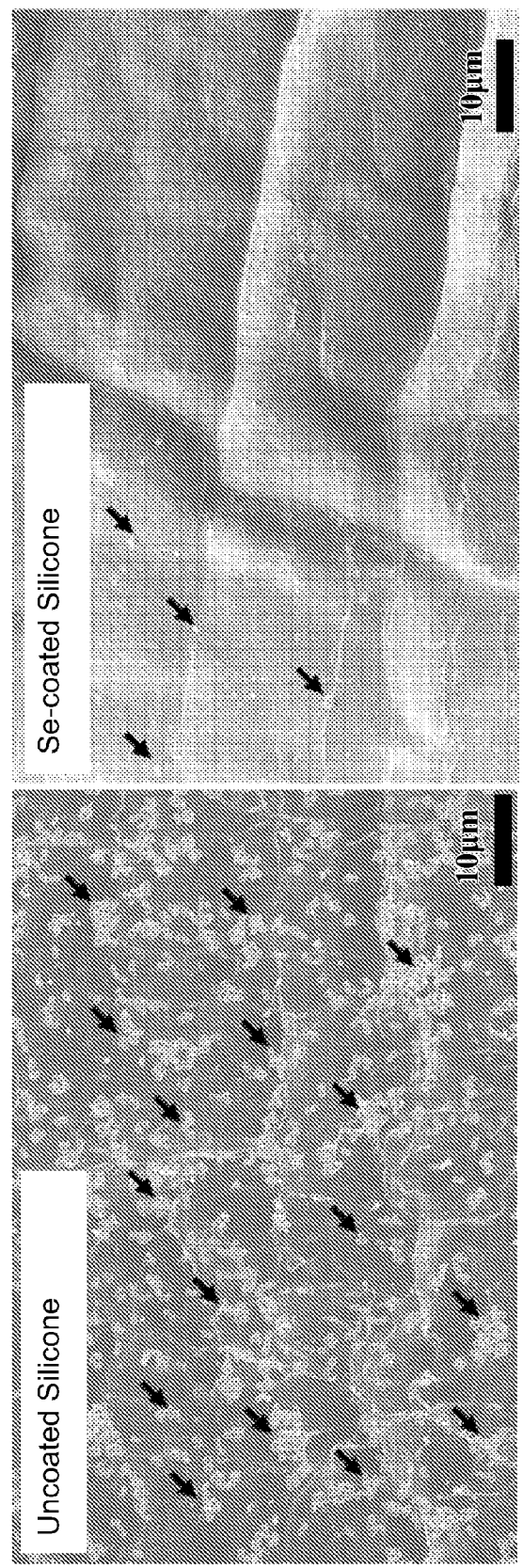
FIG. 8 depicts SEM images of uncoated (left) and selenium-coated (right) silicone substrates after inoculation for 8 hours at a seeding density of 20,000,000 S. aureus bacteria per well (24 well plate). Arrows indicate cells.
Figure 9:
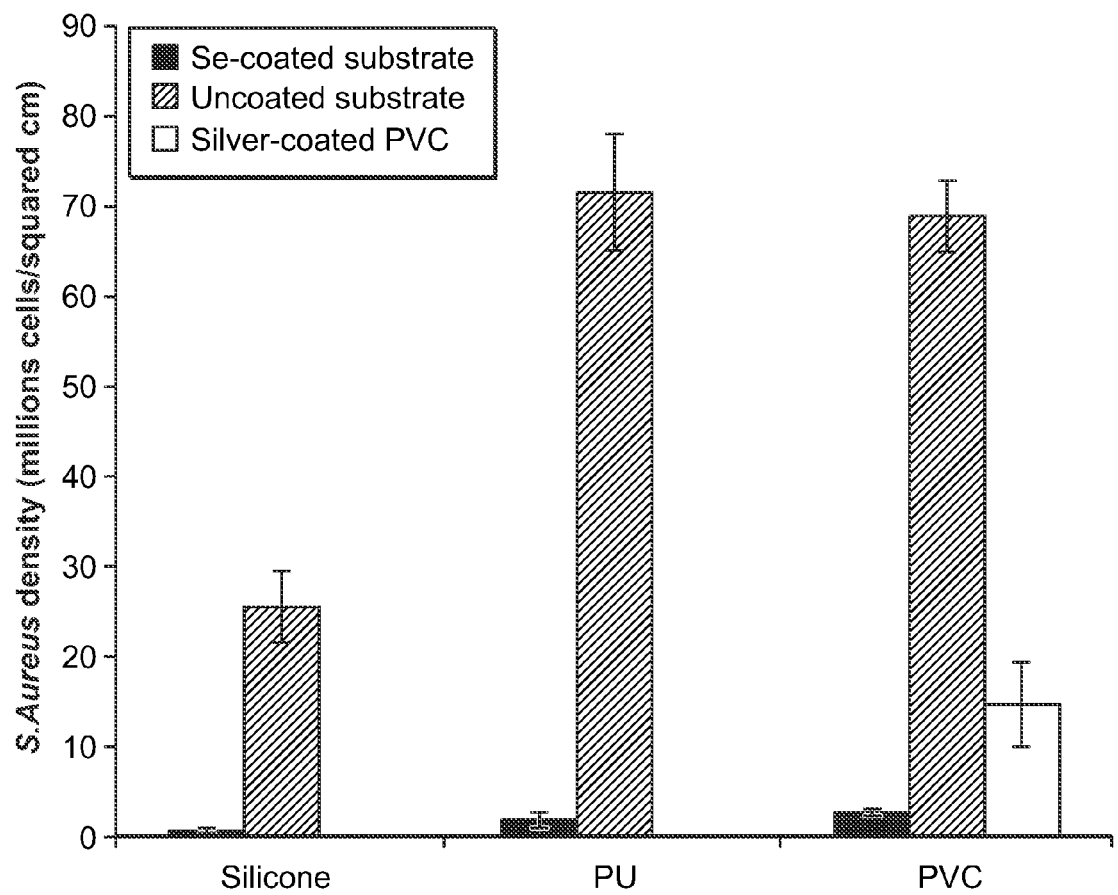
FIG. 9 is a graph depicting S. aureus attachment densities determined from SEM images on uncoated (grey bar) and selenium-nanocluster-coated (black bar) polyurethane, polyvinyl chloride and silicone substrates. Commercially available silver-coated polyvinyl chloride endotracheal tubes (white bar) are included for comparison.

Substrates with and without selenium nanoclusters were placed into the wells of 24 well plates. S. Aureus (ATCC, 25923) was then seeded in trypic soy broth at approximately 20,000,000 bacteria per well and inoculated for 8 hours in a standard bacteria culture incubator (37° C., humidified, 5% CO2, 20% O2 environment, non-shaking) After 8 hours, the substrates were removed from culture. The substrates were prepared for SEM visualized; they were rinsed in 0.1M sodium cacodylate buffer (SCB) solution, fixed in 2.5% glutaraldehyde in 0.1M SCB for 30 min at room temperature, rinsed in SCB, dehydrated in a series of ethanol solutions (30%, 50%, 70%, 90%, 95%, 100% ethanol, 10 min each), left in 100% ethanol for 15 min, critically-point dried, sputter-coated with gold and finally visualized under SEM (LEO 1530VP) with an accelerating voltage from 3 to 10 kV. FIG. 6 indicates a greatly reduced bacterial presence (arrows indicating representative bacterial cells) on the surface of the polyurethane surface including selenium nanoclusters compared to the polyurethane surface lacking selenium nanoclusters. FIG. 7 indicates a greatly reduced bacterial presence (arrows indicating representative bacterial cells) on the surface of the polyvinyl chloride surface including selenium nanoclusters compared to either the polyvinylchloride surface lacking selenium nanoclusters or the silver coated polyvinylchloride. FIG. 8 indicates a greatly reduced bacterial presence (arrows indicating representative bacterial cells) on the surface of the silicone surface including selenium nanoclusters compared to the silicone surface lacking selenium nanoclusters. FIG. 9 is a graph showing S. Aureus density for each of a substrate with selenium nanoclusters, a substrate without selenium nanoclusters and a silver coated substrate indicating that the substrate coated with the selenium nanoclusters had the lowest amount of bacteria.

Example 2

Formation of Selenium Nanoclusters on Titanium Surfaces to Reduce *S. epidermidis* Attachment and Proliferation Over a 3 Day Period Titanium substrates were degreased and sonicated in acetone and ethanol for 10 min. Cleaned titanium substrates were used as a base substrate for immersion in a colloid of a selenium precursor and a reducing agent. The substrates were exposed to 4:1 molar mixtures of glutathione and sodium selenite (Na2SeO3) in the concentration ranges below:

| Reagent | Low Density Nanoclusters | Medium Density Nanoclusters | High Density Nanoclusters |
| --- | --- | --- | --- |
| Deionized Water | 14.5 ml | 14 ml | 13 ml |
| 100 mM Glutathione | 0.25 ml | 0.5 ml | 1 ml |
| 25 mM Sodium Selenite | 0.25 ml | 0.5 ml | 1 ml |

Specifically, the cleaned substrates were first placed in a 50 ml beaker with the side intended to be deposited with the selenium nanoclusters facing upward. The reduced glutathione solution was added to the beaker followed by the sodium selenite solution. Three different solution concentrations (as shown above) were used to achieve different densities denominated as low density, medium density and high density selenium nanoclusters. After a gentle mixing of the solutions in the reaction beaker, 1 mL of 1M NaOH was introduced to bring the pH into the alkaline regime. The reaction mixture was once again gently mixed and left undisturbed for 10 min. The substrates were removed from the beaker and rinsed in deionized water. The uncoated and coated titanium substrates were exposed to ultra-violet light for 24 hours on each side to sterilize them before use in cell experiments.

Figure 10:
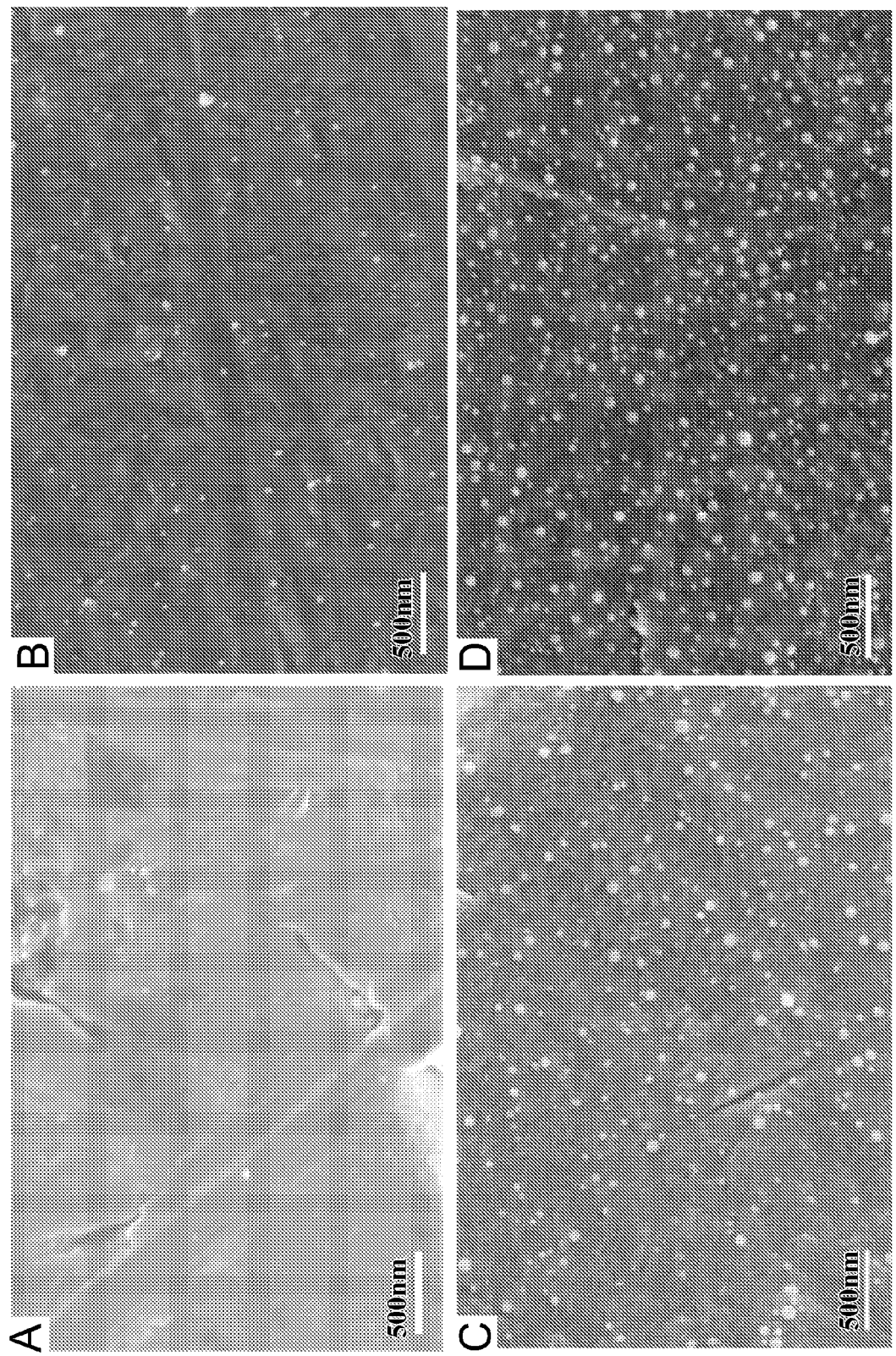
FIG. 10 depicts SEM images of (A) uncoated titanium, (B) titanium coated with a low density of selenium nanoclusters (14.5 ml deionized water, 0.25 ml each of 100 mM glutathione and 25 mM sodium selenite), (C) titanium coated with a medium density of selenium nanoclusters (14 ml deionized water, 0.5 ml each of 100 mM glutathione and 25 mM sodium selenite) and (D) titanium coated with a high density of selenium nanoclusters (13 ml deionized water, 1 ml each of 100 mM glutathione and 25 mM sodium selenite).

Surfaces of un-deposited and Se-deposited titanium substrates were visualized via SEM with an accelerating voltage from 3 kV to 10 kV (see FIG. 10). To study surface roughness of the substrates, atomic force microscopy (AFM) was used. The scanning area was 5 μm×5 μm, and each substrate was scanned at 5 random regions. FIG. 11 indicates that surface roughness increased with increasing selenium nanocluster density. FIG. 12 is a graph plotting normalized roughness verses selenium nanocluster density indicating that surface roughness increases with increasing selenium nanocluster density.

Water contact angles were measured for a titanium surface with low, medium and high concentrations of selenium nanoclusters and a titanium surface without selenium nanoclusters by placing a 2 μL drop of deionized water onto the substrates and recording the contact angles within 15 seconds. The graph in FIG. 13 shows that contact angles increased on the substrates coated with selenium nanoclusters. Thus, coating the surface with selenium nanoclusters created a more hydrophobic surface. According to the data presented in FIG. 5 and FIG. 9, the selenium nanoclusters are used to alter the surface hydrophilicity or hydrophobicity of a substrate as evidenced by an increased or decreased water contact angle relative to the surface without the selenium nanoclusters. The selenium nanoclusters can render hydrophilic surfaces more hydrophobic and hydrophibic surfaces more hydrophilic by imparting the properties of the selenium nanoclusters to the surface of the substrates.

Centrifuge tubes were prepared with 3 ml Luria broth (LB) and inoculated with *S. epidermidis* (ATCC 35984) with a sterile loop followed by agitation until the bacteria culture reached stationary phase (about 18 hours). At that point, cells were diluted in LB to an optical density of 0.52 at 562 nm using a microplate reader. This value was equivalent to 30% absorbance correlating to a three on the McFarland Scale, or $9\times10^8$ bacteria per ml. Bacteria were further diluted and titanium substrates were seeded with $1.5\times10^6$ cells/cm$^2$. After 3 days of inoculation, the titanium substrates were put into 15 ml centrifuge tubes followed by vortexing and sonicating to collect cells. 200 μl of each medium containing cells was placed into a well of a 96 well plate and analyzed for cell concentration using a spectrophotometer. Light absorbance was measured at 562 nm. The graph in FIG. 14 shows that the low, medium and high density selenium nanoclusters reduced *S. epidermidis* optical densities relative to the titanium substrate without the selenium nanoclusters.

Example 3

Selenium Nanoclusters Cause *S. aureus* Death

*S. aureus* was cultured in the supernatant from either uncoated PVC or selenium coated PVC substrates to determine whether selenium nanoclusters caused intracellular thiol depletion in *S. aureus*. After 8 hrs of incubation, intracellular thiol levels in bacteria were determined using the Glutathione assay kit (Sigma). *S. aureus* cultured with fresh bacterial culture media (i.e., tryptic soy broth) were used as controls. As can be seen in FIG. 15, the thiol level in the bacteria cultured in the supernatant from the selenium-coated PVC was significantly lower than that of bacteria cultured in the supernatant from uncoated PVC. Without wishing to be bound by scientific theory, selenium in the selenium nanocluster coatings was released into the bacteria culture media and this released selenium induced depletion of intracellular thiol which caused bacteria death.

Example 4

Selenium Nanoparticles Inhibit Growth of Bacteria in Solution

Selenium nanoparticles were synthesized by reduction of sodium selenite (Alfa Aesar) by glutathione (reduced form, GSH, TCI America) stabilized by bovine serum albumin (BSA, Sigma Aldrich). Specifically, 3 ml of 25 mM Na$_2$SeO$_3$, 3 ml of 100 mM GSH and 0.15 g BSA were added to 9 ml double distilled water in a sterile cabinet. BSA was used as a surfactant to keep the selenium nanoparticles well dispersed. All solutions were made in a sterile environment by using a sterile cabinet and double distilled water. After the reactant solution was mixed, 1M NaOH was added to bring the pH of the solution to the alkaline regime. Selenium nanoparticles were formed immediately following the addition of NaOH as visualized by a color change of the reactant solution from clear white to clear red. Selenium nanoparticles were then collected by centrifuging at 13000 rounds per minute and were re-suspended in deionized water five times before using in bacteria experiments.

The size and morphology of selenium nanoparticles were investigated using a transmission electron microscope (TEM). For this, the dispersions of nanoparticles in deionized water were allowed to slowly dry on formvar-coated copper grids. All imaging was carried out using a Philips 410 TEM (New York, N.Y., USA) at 80 kV.

The size distribution of selenium nanoparticles was investigated by dynamic light scattering (DLS) technique using a Zetasizer-Nano-S90 (Malvern Instrument). Chemistry of selenium nanoparticles was characterized using X-ray photoelectron spectroscopy (XPS, Perkin-Elmer PHI. 5500 Multi-Technique System). For this, a drop of selenium nanoparticle solution was placed on a glass coverslip, air-dried and analyzed under XPS.

TEM images of selenium nanoparticles show that the particles were spherical and about 40-100 nm in diameter (FIG. 16). Further investigation of size distribution of the selenium nanoparticles by DLS revealed that most of the particles had diameters of 100 nm (FIG. 17). The sizes observed by DLS were larger than those determined by TEM images because water molecules bound to the surface of the nanoparticles created a "hairy layer" that made the particles appear larger.

A bacterial cell line of biofilm-producing *S. aureus* was obtained in freeze-dried form from the American Type Culture Collection (catalog number 25923). The cells were propagated in 30 mg/mL tryptic soy broth (TSB, MP Biomedicals). A sterile loop was used to withdraw some of the bacteria from the frozen vial, streaked onto tryptic soy agar plates (30 g Tryptone [MP Biomedicals] and 15 g agar [Sigma] per litter of distilled water) and incubated for 12 hrs. Another sterile loop was used to select one colony from the agar plates to place into 3 ml trypic soy broth (TSB, 30 g/L) and was incubated for 16 hrs. Bacteria concentration was assessed by measuring optical density of bacterial solution at 562 nm and using a standard curve correlating optical densities and bacterial concentrations. The bacterial solution was prepared at a concentration of 50,000 cells/mL for all experiments.

Three concentrations of selenium (Se) nanoparticles were tested against *S. aureus* growth: 3.1 µg Se/mL, 6.2 µg Se/mL and 12.5 µg Se/mL with TSB (0 µg Se/mL) as the control. Selenium nanoparticles were mixed with bacterial solutions and cultured for 4, 12 and 24 hrs in an incubator (37° C., humidified, 5% $CO_2$) shaking at 250 rounds per minute. Blank solutions were prepared by adding selenium nanoparticles into TSB without bacteria at the above concentrations of particles. Blank solutions of TSB without bacteria and without selenium nanoparticles were used as the blank for the controls. When the selenium nanoparticles were mixed with the bacterial solution, the growth of bacteria was significantly inhibited after 4 hrs (compared to the controls—0 µg/mL). The inhibitory effects continued after 24 hrs (FIG. 18). A dose-dependent inhibition of bacterial growth was observed at 4 hrs and 12 hrs.

At the end of the prescribed time periods, optical densities (or the degree of "cloudiness") of the bacteria solutions (which is proportional to bacteria densities) were measured. For this, 200 µL of the bacteria solution, control, or blank were added to wells of a 96 well plate and optical densities were measured at 562 nm. Measured optical densities of bacterial solutions were subtracted by that of the corresponding blanks to remove the optical density resulting from the nanoparticles alone.

*S. aureus* (at a density of ~50,000 cells/mL) were cultured with selenium nanoparticles (at a concentration of 3.1 µg/mL in tryptic soy broth) for 4 hrs under standard conditions (37° C., 5% $CO_2$, 95% humidified air) shaking at 250 rounds per minute. After the indicated time, cells were collected and analyzed for thiol content using a glutathione assay kit (CS1020, Sigma Aldrich) following manufacturer's instruction. *S. aureus* cultured in normal cell culture media without selenium nanoparticles were used as a control. The glutathione assay kit uses a thiol probe (monochlorobimane) which passes through cell membranes to detect the level of glutathione, the major free thiol in most living cells. Glutathione is involved in many biological processes such as removal of hydroperoxides and detoxification of xenobiotics. Intracellular reduced glutathione level is a sensitive indicator of the overall health of a cell. If the probe binds to reduced glutathione in cells, it forms a fluorescent product whose fluorescence intensity can be measured. The unbound probe does not show fluorescence. Thiol assays were conducted to determine thiol content in *S. aureus* cultured with selenium nanoparticles. *S. aureus* cultured in normal bacteria culture media (tryptic soy broth (TBS)) were used as the control. The results (FIG. 19) showed that the intracellular thiol levels in *S. aureus* cultured with selenium nanoparticles was significantly decreased (to approximately 90% of the control) compared to that of the control. This means that *S. aureus* treated with selenium nanoparticles had depleted thiol levels which is known to cause cell death.

Example 5

Selenium Nanoclusters Inhibit Growth of Yeast

PVC substrates with or without selenium nanoclusters were contacted with *C. albicans* and cultured according to methods known in the art. The amount of *C. albicans* was then determined for the uncoated PVC and the PCV coated with selenium nanoclusters. As can be seen in FIG. 20, the PVC coated with selenium nanoclusters significantly inhibited the growth and/or proliferation of *C. albicans*.

All experiments were conducted in triplicate and repeated three times. Data were collected and the significant differences were assessed with the probability associated with one-tailed Student's t tests.

What is claimed is:

1. A method of inhibiting growth of a microbial, bacterial, fungal or yeast pathogen comprising contacting the pathogen to elemental selenium nanoclusters and inhibiting growth of the pathogen.

2. The method of claim 1 wherein the pathogen is on a substrate.

3. The method of claim 2 wherein the substrate includes a metal, a polymer, a ceramic or composites thereof.

4. The method of claim 3 wherein the metal is titanium, aluminum, platinum, niobium, tantalum, tin, nickel, cobalt, chromium, molybdenum, stainless steel, nitinol, Ti6Al4V, SiN, CoCrMo, zinc, silver, gold or alloys thereof.

5. The method of claim 3 wherein the polymer is polycarbonate, polyethyleneimine, isoplast, polyvinyl chloride, silicone, polyurethane, polyether imide, polycaprolactone, poly-lactic-co-glycolic acid, poly-lactic acid, poly-glycolic acid, polyethylene, polyethylene glycol, polydimethylsiloxane, polyacrylamide, polypropylene, polystyrene, polyether ether ketone (PEEK), ultra high molecular weight polyethylene (UHMWPE), hydrogels, or composites thereof.

6. The method of claim 3 wherein the ceramic is alumina, titania, hydroxyapatite, silica, calcium phosphates, bone cements, metal oxides or composites therefore.

7. A method of increasing the antimicrobial, antibacterial, antifungal or anti-yeast properties of a substrate comprising depositing selenium nanoclusters onto a substrate by contacting the substrate with a selenium precursor and a reducing agent for a time sufficient to form selenium nanoclusters on a surface of the substrate.

8. The method of claim 7 wherein the substrate includes a metal, a polymer, a ceramic or composites thereof.

9. The method of claim 8 wherein the metal is titanium, aluminum, platinum, niobium, tantalum, tin, nickel, cobalt, chromium, molybdenum, stainless steel, nitinol, Ti6Al4V, SiN, CoCrMo, zinc, silver, gold or alloys thereof.

10. The method of claim 8 wherein the polymer is polycarbonate, polyethyleneimine, isoplast, polyvinyl chloride, silicone, polyurethane, polyether imide, polycaprolactone, poly-lactic-co-glycolic acid, poly-lactic acid, poly-glycolic acid, polyethylene, polyethylene glycol, polydimethylsiloxane, polyacrylamide, polypropylene, polystyrene, polyether ether ketone (PEEK), ultra high molecular weight polyethylene (UHMWPE), hydrogels, or composites thereof.

11. The method of claim 8 wherein the ceramic is alumina, titania, hydroxyapatite, silica, calcium phosphates, bone cements, metal oxides or composites therefore.

12. The method of claim 7 wherein the selenium precursor is sodium selenite or selenious acid.

13. The method of claim 7 wherein the reducing agent is glutathione, hydrazine, dextrose, ascorbic acid or sodium ascorbate.

14. A method of inhibiting growth of a microbial, bacterial, fungal or yeast pathogen on the surface of a substrate comprising providing the surface of the substrate with elemental selenium nanoclusters, contacting the surface with the pathogen and inhibiting growth of the pathogen on the surface.

15. A method of reducing a microbial, bacterial, fungal or yeast pathogen infection in an animal comprising inserting into the animal a substrate having a surface including elemental selenium nanoclusters, contacting the surface with a microbial, bacterial, fungal or yeast pathogen and inhibiting growth of the pathogen on the surface.

* * * * *